United States Patent
Mireles et al.

(10) Patent No.: US 11,218,668 B2
(45) Date of Patent: Jan. 4, 2022

(54) VIDEO CONFERENCING METHOD

(71) Applicant: Present Communications, Inc., Redwood City, CA (US)

(72) Inventors: Matt Mireles, Redwood City, CA (US); Yousif Astarabadi, Redwood City, CA (US); Shaun Astarabadi, Redwood City, CA (US); Emil Romanus, Redwood City, CA (US); Kristina Nikkhah, Redwood City, CA (US)

(73) Assignee: Present Communications, Inc., Redwood City, CA (US)

( * ) Notice: Subject to any disclaimer, the term of this patent is extended or adjusted under 35 U.S.C. 154(b) by 0 days.

(21) Appl. No.: 17/192,828

(22) Filed: Mar. 4, 2021

(65) Prior Publication Data

US 2021/0195142 A1 Jun. 24, 2021

Related U.S. Application Data

(63) Continuation of application No. 16/870,010, filed on May 8, 2020, now Pat. No. 10,958,874.

(60) Provisional application No. 62/845,781, filed on May 9, 2019.

(51) Int. Cl.
*H04N 7/15* (2006.01)
*G06T 11/20* (2006.01)

(52) U.S. Cl.
CPC .............. *H04N 7/15* (2013.01); *G06T 11/20* (2013.01)

(58) Field of Classification Search
CPC ................................. H04N 7/15; G06T 11/20
See application file for complete search history.

(56) References Cited

U.S. PATENT DOCUMENTS

| | | | | |
|---|---|---|---|---|
| 10,958,874 | B2* | 3/2021 | Astarabadi | H04N 7/15 |
| 2012/0236105 | A1* | 9/2012 | Alberth | H04N 7/147 348/14.07 |
| 2015/0042743 | A1* | 2/2015 | Cullen | G06K 9/00221 348/14.02 |
| 2019/0222807 | A1* | 7/2019 | Rivard | G10L 21/10 |
| 2019/0342507 | A1* | 11/2019 | Dye | H04N 7/141 |
| 2021/0042508 | A1* | 2/2021 | Matula | G06K 9/00248 |
| 2021/0049468 | A1* | 2/2021 | Karras | G06N 3/08 |
| 2021/0111916 | A1* | 4/2021 | Velayutham | H04L 12/1818 |

\* cited by examiner

*Primary Examiner* — Stella L. Woo
(74) *Attorney, Agent, or Firm* — Run8 Patent Group, LLC; Peter Miller; Alexander Rodriguez

(57) ABSTRACT

One variation of a method for video conferencing includes, during a setup period: accessing a test video feed; and generating a face model, representing facial characteristics of a first user depicted in the test video feed, based on features detected in the test video feed. The method also includes, during an operating period: accessing a video feed; representing constellations of facial landmarks, detected in frames in the video feed, in a feed of facial landmark containers; representing sets of facial muscle actions, detected in frames in the video feed, in a feed of facial expression containers; and transforming the feed of facial landmark containers, the feed of facial expression containers, and the face model into a feed of synthetic face images according to the synthetic face generator.

20 Claims, 7 Drawing Sheets

VIDEO CONFERENCING METHOD

CROSS-REFERENCE TO RELATED APPLICATIONS

This application is a continuation-in-part of U.S. patent application Ser. No. 16/870,010, filed on 8 May 2020, which claims the benefit of U.S. Provisional Application No. 62/845,781, filed on 9 May 2019, each of which is incorporated in its entirety by this reference.

TECHNICAL FIELD

This invention relates generally to the field of video conferencing and more specifically to a new and useful method for synthetic video reconstruction in the field of video conferencing.

DESCRIPTION OF THE EMBODIMENTS

The following description of embodiments of the invention is not intended to limit the invention to these embodiments but rather to enable a person skilled in the art to make and use this invention. Variations, configurations, implementations, example implementations, and examples described herein are optional and are not exclusive to the variations, configurations, implementations, example implementations, and examples they describe. The invention described herein can include any and all permutations of these variations, configurations, implementations, example implementations, and examples.

1. Method

Figure 1:
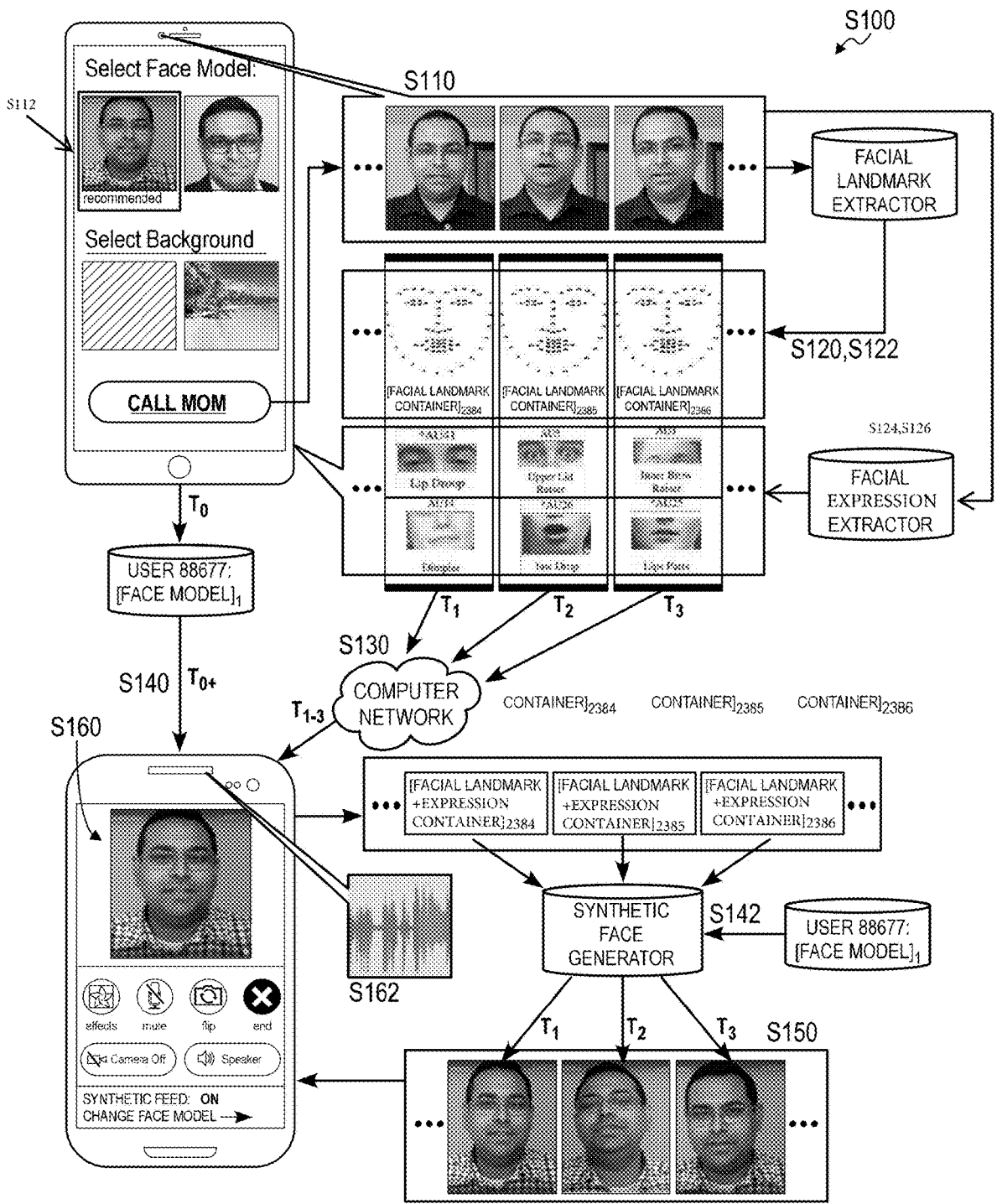
FIG. 1 is a flowchart representation of a method.

As shown in FIG. 1, a method S100 for video conferencing includes, during a setup period: accessing a target image of a first user; detecting a target face in the target image; representing a target constellation of facial landmarks, detected in the target image, in a target facial landmark container; representing a target set of facial muscle actions, detected in the target image, in a target facial expression container; generating a target set of face model coefficients; transforming the target facial landmark container, the facial expression container, and the target set of face model coefficients into a target synthetic face image according to a synthetic face generator; characterizing a difference between the target synthetic face image and the target face detected in the target image; adjusting the target set of face model coefficients to reduce the difference; and generating a first face model, associated with the first user, based on the target set of face model coefficients in Block S104. The method S100 further includes, during an operating period succeeding the setup period: accessing a first video feed depicting the first user in Block S110; for a first frame, in the first video feed, captured at a first time, detecting a first constellation of facial landmarks in the first frame in Block S120, representing the first constellation of facial landmarks in a first facial landmark container in Block S122, detecting a first set of facial muscle actions in the first frame in Block S124, and representing the first set of facial muscle actions in a first facial expression container in Block S126; and transforming the first facial landmark container, the first facial expression container, and the first face model into a first synthetic face image according to the synthetic face generator in Block S150.

One variation of the method S100 shown in FIG. 1 includes, during a setup period: accessing a first video feed captured by a first device interfacing with the first user; and generating a first face model, representing facial characteristics of a first user depicted in the first video feed, based on features detected in the first video feed in Block S104. This variation of the method S100 further includes, during an operating period: accessing a second video feed in Block S110; representing constellations of facial landmarks, detected in frames in the second video feed, in a second feed of facial landmark containers in Block S122; representing sets of facial muscle actions, detected in frames in the second video feed, in a second feed of facial expression containers in Block S126; and transforming the second feed of facial landmark containers, the second feed of facial expression containers, and the first face model into a second feed of synthetic face images according to the synthetic face generator in Block S150.

Another variation of the method S100 shown in FIG. 1 includes, during a setup period: accessing a photographic image depicting a first user; generating a first face model, representing facial characteristics of the first user, based on features detected in the photographic image; and storing the first face model in a database of face models of the first user in Block S104. This variation of the method S100 also includes, during an operating period: receiving a selection of the first face model, in the database of face models, from the first user in Block S112; accessing a first video feed in Block Silo; representing constellations of facial landmarks, detected in frames in the first video feed, in a first feed of facial landmark containers in Block S122; representing sets of facial muscle actions, detected in frames in the first video feed, in a first feed of facial expression containers in Block S126; and transforming the first feed of facial landmark containers, the first feed of facial expression containers, and the first face model into a first feed of synthetic face images according to the synthetic face generator in Block S150.

As shown in FIGS. 2A-2D, another variation of the method includes, at a first device associated with a first user: capturing a first video feed in Block S110; for a first frame, in the first video feed, captured at a first time, detecting a first constellation of facial landmarks in the first frame in Block S120 and representing the first constellation of facial landmarks in a first facial landmark container in Block S122; and transmitting the first facial landmark container and a first audio packet, captured at approximately (e.g., within 50 milliseconds of) the first time, to a second device in Block S130. The method also includes, at the second device associated with a second user: accessing a first face model representing facial characteristics of the first user in Block S140; accessing a synthetic face generator in Block S142; transforming the first facial landmark container and the first face model into a first synthetic face image according to the synthetic face generator in Block S150; rendering the first synthetic face image at a second time in Block S160; and outputting the first audio packet at approximately (e.g., within 50 milliseconds of) the second time in Block S162.

As shown in FIGS. 2A-2D, one variation of the method includes, at a first device associated with a first user:

capturing a first video feed in Block S110; representing constellations of facial landmarks, detected in the first video feed, in a first feed of facial landmark containers in Block S122; and transmitting the first feed of facial landmark containers to a second device in Block S130. This variation of the method also includes, at the second device associated with a second user: accessing a first face model representing facial characteristics of the first user in Block S140; accessing a synthetic face generator in Block S142; transforming the first feed of facial landmark containers and the first face model into a first feed of synthetic face images according to the synthetic face generator in Block S150; and rendering the first feed of synthetic face images in Block S152.

As shown in FIGS. 2A-2D, another variation of the method includes, at a first device associated with a first user: capturing a first video feed in Block S110; for a first frame, in the first video feed, captured at a first time, detecting a first constellation of facial landmarks in the first frame in Block S120 and representing the first constellation of facial landmarks in a first facial landmark container in Block S122; and transmitting the first facial landmark container and a first audio packet, captured at approximately the first time, to a second device in Block S130. This variation of the method also includes, at the second device associated with a second user: accessing a first face model representing facial characteristics of the first user in Block S140; accessing a synthetic face generator in Block S142; transforming the first facial landmark container and the first face model into a first synthetic face image according to the synthetic face generator in Block S150; rendering the first synthetic face image at a second time in Block S160; outputting the first audio packet at approximately (e.g., within 50 milliseconds of) the second time in Block S162; capturing a second video feed in Block S110; for a second frame, in the second video feed, captured at approximately (e.g., within one second of) the first time, detecting a second constellation of facial landmarks in the second frame in Block S120 and representing the second constellation of facial landmarks in a second facial landmark container in Block S122; and transmitting the second facial landmark container to the first device in Block S130. This variation of the method further includes, at the first device: accessing a second face model representing facial characteristics of the second user in Block S140; accessing the synthetic face generator in Block S142; transforming the second facial landmark container and the second face model into a second synthetic face image according to the synthetic face generator in Block S150; and rendering the second synthetic face image at approximately (e.g., within one second of) the second time in Block S152.

2. Applications

Generally, Blocks of the method can be executed by native or browser-based applications executing on a set of computing devices (e.g., smartphones, tablets, laptop computers) during a video call between two users in order: to compress a first video feed of a first user into a first lightweight (e.g., sub-kilobyte) feed of constellations of facial landmarks and facial expression encodings at a first device; and to reconstruct this first video feed at a second device by injecting this first feed of facial landmark constellations and facial expression encodings and a first (pseudo-) unique face model of the first user into a first instance of a synthetic face generator, which outputs a first stream of synthetic, photorealistic, emotion-authentic images of the first user that the second device then renders in near real-time.

Simultaneously, the second device can compress a second video feed of the second user into a second lightweight constellation of facial landmarks and facial expression encodings; and the first device can reconstruct this second video feed by injecting this second feed of facial landmark constellations and facial expression encodings and a second (pseudo-) unique face model of the second user into a second instance of the synthetic face generator, which outputs a second stream of synthetic, photorealistic, emotion-authentic images of the second user that the first device then renders in near real-time.

2.1 Bandwidth

In particular, rather than transmit and receive data-rich video feeds during a video call, a first device executing Blocks of the method can instead: extract facial landmark constellations from a first video feed captured at the first device; package these facial landmark constellations into facial landmark containers; detect actions of individual muscles or muscle groups in the first user's face detected in the first video feed; encode these muscle actions (and their intensities) in separate facial expression containers (or append values representing these muscle actions and intensities to concurrent facial landmark containers); and transmit a first feed of facial landmark containers and/or a first feed of facial expression containers to the second device. The second device can then: leverage a local copy of the synthetic face generator and a local copy of a first face model associated with the first user to transform the first feed of facial landmark containers and facial expression containers into a photorealistic representation of the first user's face; and render this first photorealistic synthetic video feed in near real-time.

Concurrently, the second device—also executing Blocks of the method—can: extract facial landmark containers from a second video feed captured at the second device; encode muscle actions (and their intensities) detected in the second video feed in separate facial expression containers (or append values representing these muscle actions and intensities to concurrent facial landmark containers); and transmit a second feed of facial landmark containers and/or a second feed of facial expression containers to the first device. The first device can then: leverage a local copy of the synthetic face generator and a local copy of a second face model associated with the second user to transform the second feed of facial landmark containers and/or the second feed of facial expression containers into a photorealistic representation of the second user's face; and render this second photorealistic synthetic video feed in near real-time.

The second user may thus experience the video call as though a color video was received from the first user's device—and vice versa—without necessitating a consistent, high-bandwidth, low-latency data connection between the first and second devices.

More specifically, by extracting facial landmark containers and facial expression containers from a high(er)-definition video feed according to the method, the first device can compress this high(er)-definition video feed by multiple orders of magnitude (e.g., by approximately 100 times). Transmission of a feed of facial landmark and/or expression containers—at a natural frame rate of the original high(er)-definition video (e.g., 24 frames per second)—from the first device to the second device during a video call may therefore require significantly less bandwidth than the original high-definition video (e.g., less than 10 kilobits per second rather than 1.5 Megabits per second). The second device can: then reconstruct the first video feed of the first user by passing a local copy of a (pseudo)-unique face model of the first user, a first feed of facial landmark containers, and/or a first feed of facial expression containers—received from the first device—into a synthetic face generator, which generates and outputs a stream of synthetic, photorealistic images of the first user's face in near real-time (e.g., in less than 100 milliseconds or within as little as 30 milliseconds of a receipt of each subsequent facial landmark and expression container pair from the first device); and render this stream of synthetic, photorealistic images of the first user's face.

Therefore, the first and second devices can execute Blocks of the method to support consistent, high-quality video—with significantly less upload and download bandwidth and without loss of realism, loss of authenticity of facial expressions, or loss of representation of human facial movements—during a video call.

2.2 Latency

Furthermore, humans may perceive audible and visual events temporally offset by up to 200 milliseconds as occurring concurrently. However, the first and second devices can cooperate to rapidly execute Blocks of the method. For example, the first device can: capture a video frame; generate first facial landmark container representing a first facial landmark constellation detected in this video frame; generate a first facial expression container representing a muscle actions of the first user's face detected in this video frame; and upload this first facial landmark and expression container pair to a computer network within 50 milliseconds. The second device can then: download this facial landmark and expression container pair; inject this facial landmark and expression container pair and a stored local copy of a first face model of the first user into a local copy of the synthetic face generator to generate a synthetic face image; overlay the synthetic face image on a static or animated background frame to generate a synthetic video frame; and render the synthetic video frame on a display of the second device within 150 milliseconds of receipt of the facial landmark container.

Generally, the first device compresses a video feed (e.g., by orders of magnitude) into: a stream of facial landmark containers (e.g., each facial landmark container in the form of a vector containing 68 (x,y) coordinates for 68 predefined facial landmarks); and a stream of facial expression containers (e.g., each facial expression container in the form of a vector containing intensities of up 28 main action units or 100 main action, head movement, and eye movement action units). (Alternatively, the first device can compress a video feed into a stream of facial landmark containers, wherein each facial landmark container includes a vector containing: 68 (x,y) coordinates for 68 predefined facial landmarks; and intensity values of 28 main action units (100 main action, head movement, and eye movement action units).

Accordingly, the packet size for facial landmark containers transmitted from the first device to the second device may be relatively very small. Therefore, throughput requirements to transmit this stream of facial landmark and expression container pairs between the first and second devices over wireless and local area networks may be significantly less than actual throughputs supported by these networks. More specifically, transmission of this lightweight stream of facial landmark and expression container pairs from the first device to the second device may represent a relatively small portion of the total duration of time from capture of a video frame at the first device to reconstruction and rendering of a corresponding synthetic video frame at the second device. Accordingly, this stream of facial landmark and expression container pairs may not (or may very rarely) approach throughput limitations of these networks, thereby enabling these networks to transmit this lightweight stream of facial landmark and expression container pairs from the first device to the second device with low latency, low packet loss, and high consistency despite changes in traffic between other devices connected to these networks and even during periods of high traffic on these networks.

2.3 Realism

By executing Blocks of the method, the first and second devices can render authentic, photorealistic representations of the second and first users, respectively, during a video call—such as relative to cartoons, avatars, or caricatures that may lose authenticity and integrity due to compression and simplification of user facial expressions.

For example, the first device and/or a remote computer system (e.g., a remote server, a computer network) can: access an image (e.g., a digital photographic image, a frame from a video clip) of the first user; detect the first user's face in this image; implement a standard or generic facial landmark extractor to detect and extract a facial landmark constellation; represent this facial landmark constellation in a facial landmark container; implement a standard or generic facial expression extractor to detect actions of individual muscles or muscle groups in the face detected in this image; encode these muscle actions (and their intensities) in a set of values in a separate facial expression container; initialize a first face model containing an initial set of coefficients (or "weights"); pass this facial landmark container, the facial expression container, and the initial face model into a synthetic face generator to generate an initial synthetic face image; characterize a difference between this initial synthetic face image and the first user's face depicted in the image; and iteratively adjust coefficients in the first face model such that insertion of this first face model, the facial landmark container, and the facial expression container into the synthetic face generator produces synthetic face images with smaller differences from the first user's face depicted in the image. Once a difference between a synthetic face image is thus produced according to the first face model and the first user's face depicted in the image falls below a threshold difference, the first device or the remote computer system can store this first face model in association with the first user, such as in an account or profile associated with the user.

In this example, the first device and/or the remote computer system can implement this process when the first user creates an account within a first instance of the native or browser-based video conferencing application executing on the first device, during a setup period just before starting a video call with the second device, or after starting a video call with the second device. Additionally or alternatively, the first device (or the remote computer system) can repeat this process for additional images or video clips of the first user (e.g., depicting the first user with various facial expressions and from various perspectives) and fuse face models thus calculated for these additional images or video clips into a single, more robust face model of the user.

The first device (or the remote computer system) can then share this face model—specific to the first user—with a second device before or during a video call. During this video call, the first device can also capture a video frame via an integrated or connected camera, extract a facial landmark container and a facial expression container from this video frame, and stream this facial landmark and expression containers to the second device. The second device can then implement this face model to transform these facial landmark and expression containers into a synthetic, photorealistic image of the first user's face, which authentically replicates a facial expression of the first user, a mouth shape of the first user, an eye position of the first user, facial muscle actions in the first user's face, and a position of the first user relative to the camera at a time that the camera captured the video frame.

Therefore, though the first device streams a feed of facial landmark and expression containers to the second device rather than a live video feed of photographic video frames, the second device can leverage the face model of the first user and the synthetic face generator to generate a photorealistic feed of synthetic images that: depict—for the second user—the first user according to the first look model selected for the video call by the first user; and authentically reproduce the first user's facial expression, mouth shape, eye position, facial muscle actions, and position relative to the first device, etc. during this video call.

2.4 Devices

The method is described herein as executed by instances of a video conferencing application (hereinafter the "application"), such as a native video conferencing application or a browser application operable within a web browser executing on a device, such as a smartphone, tablet, or laptop computer. However, the method can be similar executed by devices hosting a live multi-party virtual reality experience, an asynchronous image or video chat, etc.

Furthermore, Blocks of the method are described herein as executed: by a first device to transform a first live video feed of a first user into facial landmark containers and to stream facial landmark containers to a second device; and by a second device to reconstruct and render a photorealistic, synthetic representation of the first video feed for viewing by a second user. However, the second device can simultaneously transform a second live video feed of the second user into facial landmark containers and stream facial landmark containers to the first device; and the first device can simultaneously reconstruct and render a photorealistic, synthetic representation of the second video feed for viewing by the first user.

Furthermore, the method is described herein as implemented by consumer devices to host a two-way video call between two users. However, the method S100 can be similarly implemented by a device to host one-way live video distribution, or asynchronous video replay. Additionally or alternatively, Furthermore, the method can be executed by multiple devices to host a multi-way video call between multiple (e.g., three, ten) users.

2.5 2D v. 3D

The method is described herein as executed by an instance of the video conferencing application to: capture or access a two-dimensional live video frame; extract a two-dimensional constellation of facial landmarks from this two-dimensional live video frame; extract emotion and/or expression signals from this two-dimensional live video frame; and transmit the two-dimensional constellation of facial landmarks and emotion and/or expression signals to a second device, which reconstructs a two-dimensional synthetic face image in real-time based on these data and a look model of a user.

However, the method can be similarly executed by an instance of the video conferencing application to: capture or access a three-dimensional live video frame; extract a three-dimensional constellation of facial landmarks (e.g., in an (x,y,z) or (azimuth, altitude, range) 3D location format) from this three-dimensional live video frame; extract emotion and/or expression signals from this three-dimensional live video frame; and transmit the three-dimensional constellation of facial landmarks and emotion and/or expression signals to a second device, which reconstructs a two- or three-dimensional synthetic face image in real-time based on these data and a look model of a user.

3. Facial Landmark Extractor

Figure 4:
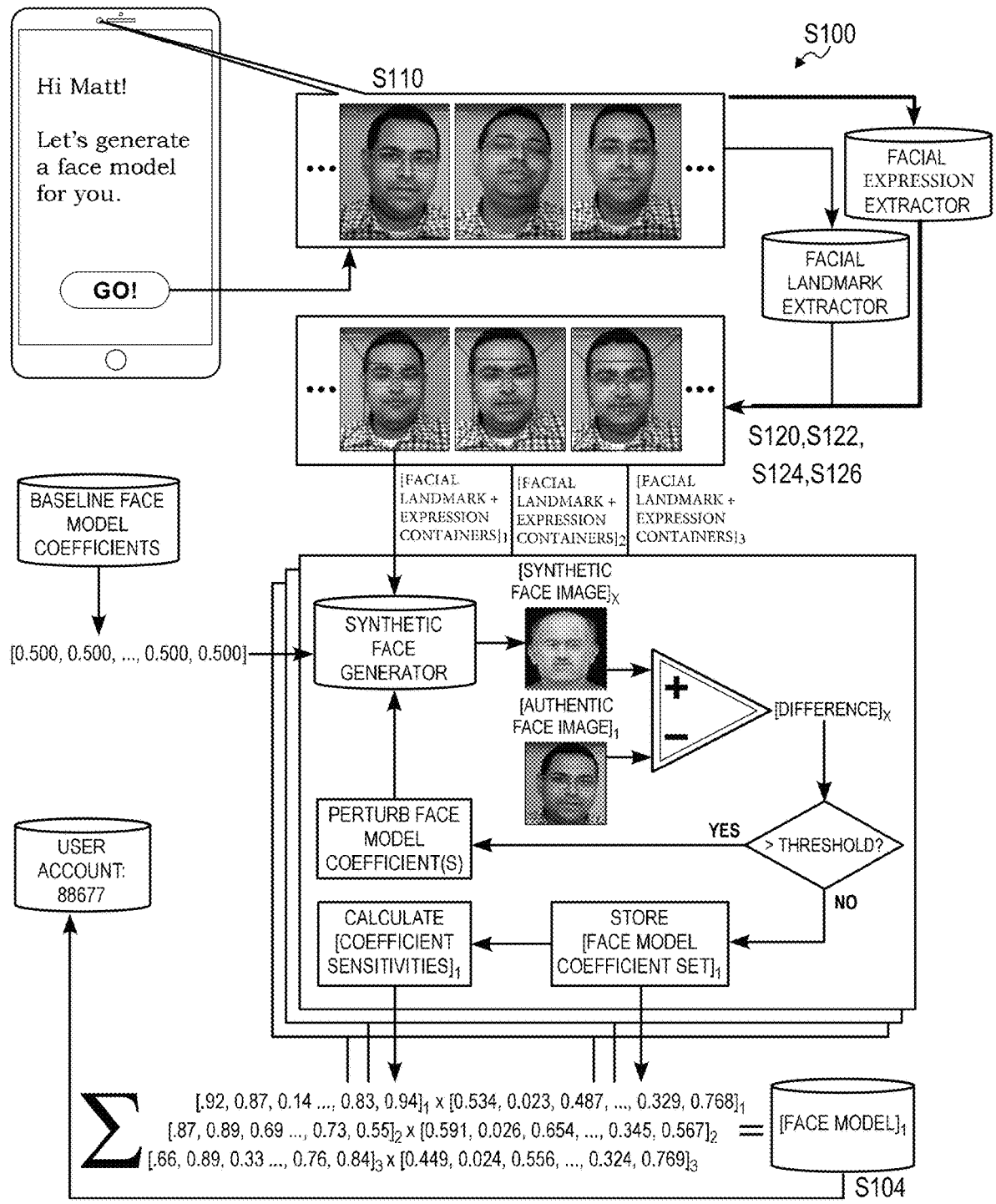
FIG. 4 is a flowchart representation of one variation of the method.

Generally, a device executing the application and/or the remote computer system can implement a facial landmark extractor: to detect a face in a region of an image (e.g., a photographic image, a frame in a video clip, and/or a frame in a live video feed); to scan this region of the image for features analogous to predefined facial landmark types; and to represent locations, orientations, and/or sizes, etc. of these analogous features—detected in the region of the image—in one facial landmark container. In particular, the device and/or the remote computer system can implement the facial landmark extractor to detect spatial characteristics of a face—such as including positions of eye corners, a nose tip, nostril corners, mouth corners, end points of eyebrow arcs, ear lobes, and/or a chin—depicted in a 2D image; and to represent these spatial characteristics in a single container (e.g., a vector, a matrix) in Block S120, as shown in FIGS. 1 and 4. For example, the device and/or the remote computer system can implement facial landmark detection to extract a facial landmark container: from a video frame during generation of a face model for a user (e.g., during initial setup of the user's account); from a photographic image during generation of a "look model" for the user; and/or from a video frame for transmission to a second device during a video call.

In one implementation shown in FIGS. 1 and 4, to generate a facial landmark container from an image (or frame), the device (or the remote computer system): accesses the image; implements facial detection techniques to detect a face in a region of the image; and initializes a facial landmark container in the form of a vector of length equal to a total quantity of predefined facial landmark types (e.g., 68). Then, for a first facial landmark type in this predefined set of facial landmark types, the device: scans the region of the frame for a feature analogous to the first facial landmark type; extracts a first location (and/or a first size, first orientation) of a particular feature depicted in the image in response to identifying this particular feature as analogous to (e.g., of a similar form, relative location, relative size) the first facial landmark type according to the facial landmark extractor in Block S120; and then writes this first location (and/or first size, first orientation) of the particular feature to a first position in the vector corresponding to the first facial landmark type in Block S122. Similarly, for a second facial landmark type in this predefined set of facial landmark types, the device: scans the region of the frame for a feature analogous to the second facial landmark type in Block S120; and then writes a null value to a second position in the vector corresponding to the second facial landmark type in response to failing to identify a particular feature analogous to the second facial landmark time in the region of the image in Block S122. The device then repeats this process for each other facial landmark type in the predefined set in order to complete the facial landmark container for this image in Blocks S120 and S122.

Furthermore, in this example, the device (or the remote computer system) can generate a facial landmark container that represents a pixel position (e.g., an (x,y) coordinate) of each detected facial landmark type within the image—and not specifically the position of the facial landmark within the region of the image depicting the user's face—such that insertion of this facial landmark container and a face model of the user into a synthetic face generator: produces a synthetic face image that appears as a photographic analog of the user's face depicted in the image; and locates this synthetic face image in a position within a synthetic video frame that is analogous to the location of the user's face depicted in the image.

In one variation, the facial landmark extractor (or the device, the remote computer system) recombines facial landmarks extracted from an image to define facial edges within the image, such at the perimeter of the user's head as depicted in the frame and edges around the user's eye, brow, nose, and lips. The facial landmark extractor (or the device, the remote computer system) then stores these facial edges in the facial landmark container, such as in addition to or instead of the facial landmarks. Later, the second device can pass these facial edges—such as in addition to or instead of the facial landmarks—into the synthetic face generator to generate a synthetic face image according to the physiognomy of the user depicted in this image.

4. Facial Expression Extractor

A device executing the application and/or the remote computer system can similarly implement a facial expression extractor: to detect a face in a region of an image (e.g., a photographic image, a frame in a video clip, and/or a frame in a live video feed); to scan this region of the image for features indicative of various facial expressions in Block S124; and to represent presence and/or magnitude of these features—detected in this region of the image—in the concurrent facial landmark container or in a separate facial expression container in Block S126.

4.1 Facial Action Coding System

In one implementation, when applied to an image, the facial expression extractor: detects a face in a sector of the image; and initializes a facial expression container (e.g., an n-dimensional vector) for this image. Then, for each action unit—in a predefined set of action units representing action of human facial muscles—the facial expression extractor: detects a facial region, depicted in the sector of the frame, containing a muscle associated with the action unit; interprets an intensity of action of the muscle based on a set of features extracted from the facial region depicted in the sector of the frame; and writes the intensity of action of the muscle to a position in the facial expression container corresponding to the action unit.

More specifically, in this implementation, the facial expression extractor can: detect actions of individual muscles or groups of muscles in a face depicted in an image; derive intensities of individual active muscles or groups of active muscles detected in the image; implement a taxonomy of human facial movements to encode a set of values (or "action units" and "action unit intensities") representing these actions and intensities; and store these values in a facial expression container paired with the concurrent facial landmark container. (Alternatively, the facial expression extractor—or a device executing the facial expression extractor—can append these encoded values to the concurrent facial landmark container generated for this image, as described above.)

In one example implementation, the facial expression extractor can implement a facial action coding system to detect and represent: a "neutral" face in an image with a "0" facial action value; an inner brow raise action (e.g., from activation of the frontalis muscle) with a "1" facial action value; an outer brow raise action (e.g., from activation of the frontalis muscle) "2" facial action value; a brow lower action (e.g., from activation of the depressor glabellae, depressor supercilii, and corrugator supercilii muscles) with a "4" facial action value; an upper lid raise action (e.g., from activation of the levator palpebrae superioris and superior tarsal muscle muscles) with a "5" facial action value; a cheek raise action (e.g., from activation of the orbicularis oculi muscle) with a "6" facial action value; a lid tightening action (e.g., from activation of the orbicularis oculi muscle) with a "7" facial action value; a lips moving toward each other action (e.g., from activation of the orbicularis oris muscle) with a "8" facial action value; a nose wrinkle action (e.g., from activation of the levator labii superioris alaeque nasi muscle) with a "9" facial action value; an upper lip raise action (e.g., from activation of the levator labii superioris and caput infraorbitalis muscles) with a "10" facial action value; a nasolabial deepening action (e.g., from activation of the zygomaticus minor muscle) with a "11" facial action value; a lip corner pull action (e.g., from activation of the zygomaticus major muscle) with a "12" facial action value; a sharp lip pull action (e.g., from activation of the levator anguli oris) with a "13" facial action value; a dimple action (e.g., from activation of the buccinator muscle) with a "14" facial action value; a lip corner depress action (e.g., from activation of the depressor anguli oris) with a "15" facial action value; a lower lip depress action (e.g., from activation of the depressor labii inferiori muscle) with a "16" facial action value; a chin raise action (e.g., from activation of the mentali muscle) with a "17" facial action value; a lip pucker action (e.g., from activation of the incisivii labii superioris and incisivii labii inferioris muscles) with a "18" facial action value; a tongue show action (e.g., from activation of the muscle) with a "19" facial action value; a lip stretch action (e.g., from activation of the risorius w/platysma muscle) with a "20" facial action value; a neck tighten action (e.g., from activation of the platysma muscle) with a "21" facial action value; a lip funnel action (e.g., from activation of the orbicularis oris muscle) with a "22" facial action value; a lip tighten action (e.g., from activation of the orbicularis oris muscle) with a "23" facial action value; a lip press action (e.g., from activation of the orbicularis oris muscle) with a "24" facial action value; a lips parting action (e.g., from activation of the depressor labii inferioris muscle and relaxation of the mentalis or orbicularis oris muscle) with a "25" facial action value; a jaw drop action (e.g., from activation of the masseter muscle and relaxation of the temporalis and internal pterygoid muscles) with a "26" facial action value; a mouth stretch action (e.g., from activation of the pterygoids and digastric muscles) with a "27" facial action value; and a lip suck action (e.g., from activation of the orbicularis oris muscle) with a "28" facial action value.

In this example implementation, the facial expression extractor can detect multiple muscular actions across a face detected in an image, can encode multiple action units for this face accordingly, and/or can estimate an emotion (and/or "mood") of the face detected in this image based on these action units. For example, the facial expression extractor can detect both "6" and "12" action units described above in a face in an image, which may predict an expression of "happiness" in the face. In a similar example, the facial expression extractor can detect "1," "4," and "14" action units described above in a face in an image, which may predict an expression of "sadness" in the face. In yet another example, the facial expression extractor can detect "1," "2," "5," and "26" action units described above in a face in an image, which may predict an expression of "surprise" in the face. In another example, the facial expression extractor can detect "1," 2," "4," "5," "7," "20," and "26" action units described above in a face in an image, which may predict an expression of "fear" in the face.

Furthermore, in this example implementation, the facial expression extractor can represent intensities of action units detected in an image according to the facial action coding system, such as including: "A" for a weak trace of an action unit; "B" for a slight presence of an action unit; "C" for a marked or pronounced presence of an action unit; "D" for severe or extreme presence of an action unit; and "E" for maximum presence of an action unit. Thus, in this example, the facial expression extractor can represent a weak trace of an "inner brow raise action" detected in a face in an image with action unit "1A" and maximum presence of an "inner brow raise action" detected in a face in an image with action unit "1E."

(In this example implementation, the facial expression extractor can similarly detect and represent head movements and eye movements according to the facial action coding system.)

4.2 Facial Expression Container

Therefore, in this implementation, the facial expression extractor can: ingest an image; detect a face in the image; detect an action in one or more individual muscles or groups of muscles in the face; interpret an intensity of each detected action in Block S124; encode these actions and intensities into a set of action units and action unit intensities according to the facial action coding system; and aggregate these action units and action unit intensities into a facial expression container—paired (e.g., via like timestamps) with the facial landmark container generated from the same image by the facial landmark extractor—in Block S126.

In one example, the facial expression extractor returns a facial expression container in the form of a vector of variable length from "1" to "28," including: [0] for an image (or video frame) in which the facial expression container detects a neutral face in the image; [6, 12] for an image in which the facial expression container detects a "happy" expression on the face; [1, 4, 14] for an image in which the facial expression container detects a "sad" expression on the face; [1, 2, 5, 26] for an image in which the facial expression container detects a "surprised" expression on the face; and [1, 2, 4, 5, 7, 20, 26] for an image in which the facial expression container detects a "fearful" expression on the face.

In another example, the facial expression extractor returns a facial expression container in the form of a vector of fixed length and containing binary values representing presence of action units detected in an image, including: [1, 0, 0, 0, 0, 0, 0, 0, 0, 0, 0, 0, 0, 0, 0, 0, 0, 0, 0, 0, 0, 0, 0, 0, 0, 0, 0, 0] for an image in which the facial expression container detects a neutral face in the image; [0, 0, 0, 0, 0, 1, 0, 0, 0, 0, 0, 1, 0, 0, 0, 0, 0, 0, 0, 0, 0, 0, 0, 0, 0, 0, 0, 0] for an image in which the facial expression container detects a "happy" expression on the face; [0, 1, 0, 1, 0, 0, 0, 0, 0, 0, 0, 0, 0, 1, 0, 0, 0, 0, 0, 0, 0, 0, 0, 0, 0, 0, 0, 0] for an image in which the facial expression container detects a "sad" expression on the face; [0, 1, 1, 0, 1, 0, 0, 0, 0, 0, 0, 0, 0, 1, 0, 0, 0, 0, 0, 0, 0, 0, 0, 0, 0, 1, 0, 0] for an image in which the facial expression container detects a "surprised" expression on the face; and [0, 1, 1, 1, 1, 0, 1, 0, 0, 0, 0, 0, 0, 1, 0, 0, 0, 0, 1, 0, 0, 0, 0, 0, 0, 1, 0, 0] for an image in which the facial expression container detects a "fearful" expression on the face.

In yet another example, the facial expression extractor returns a facial expression container in the form of a vector of fixed length and containing integer values representing intensity of action units detected in an image, including: [0, 0, 0, 0, 0, 0, 0, 0, 0, 0, 0, 0, 1, 0, 1, 0, 0, 0, 0, 0, 0, 0, 0, 0, 0, 0, 0, 0] for an image in which the facial expression container detects a "contempt" expression on the face; [0, 3, 3, 0, 2, 0, 0, 0, 0, 0, 0, 0, 1, 0, 0, 0, 0, 0, 0, 0, 0, 0, 0, 0, 2, 0, 0] for an image in which the facial expression container detects a "surprised" expression on the face, wherein "0" represents an undetected action unit, "1" represents a trace intensity of an action unit, "2" represents a slight intensity of an action unit, "3" represents a marked or pronounced intensity of an action unit, "4" represents a severe or extreme intensity of an action unit, and "5" represents a maximum intensity of an action unit.

In these examples, the facial expression extractor can then write a timestamp—from the image—to the facial expression container and corresponding facial landmark container in order to link these containers as a facial landmark and expression container pair. Alternatively, the device executing the facial expression extractor can inject these action units and action unit intensities into the concurrent facial landmark container generated from the same image by the facial landmark extractor, such as by appending these action units and/or action unit intensities to this concurrent facial landmark container.

4.3 Facial Expression Extractor Construction

In the foregoing implementation, to generate the facial expression extractor, the remote computer system can: access a population of images of human faces (e.g., thousands, millions or 2D color images of human faces), each labeled with a set of action units according to the facial action coding system; and train the facial expression extractor (e.g., a conditional generative adversarial network) on this population of labeled images to detect action units in images of faces according to the facial action coding system.

4.4 Expression and Emotion Detection

Additionally or alternatively, the facial expression extractor can: detect a face in an image; and interpret a higher-order expression, emotion, and/or "mood" (e.g., happiness, sadness, fear, anger, surprise) on the face, such as by implementing an expression model to transform a set of lower-order action units detected in this image into a predominant expression, emotion, or "mood" on the face. The facial expression extractor can then return a facial expression container containing a quantitative representation of this detected expression, emotion, or "mood", such as: a first value for a type of this expression, emotion, or "mood" (e.g., "0" for a neutral expression, "1" for a happy expression, "2" for an excited expression, . . . "5" for an angry expression, and "6" for a sad expression); and a second value for an intensity of this expression, emotion, or "mood" (e.g., "1" for a weak trace of the detected expression, emotion, or "mood", "2" for a slight presence of the detected expression, emotion, or "mood", . . . , "5" for a maximum presence of the detected expression, emotion, or "mood").

However, the facial expression extractor can: detect actions of any other individual facial muscles and/or facial muscle groups in a face depicted in an image; characterize types and/or magnitudes of these muscle actions in another other way; detect or interpret present and/or magnitude of facial expressions and/or emotions in an image in any other way; and store these types and/or magnitudes of facial muscle actions, expressions, and/or emotions in any other format in the facial expression container.

4.5 Vocal Emotion Recognition

In one variation, the device executing the application and/or the remote computer system can: access an audio feed of the user's speed during a video call; implement vocal emotion recognition techniques to interpret a series of emotions exhibited by the user during the video call based audio characteristics of the user's speech; and then represent these emotions in concurrent facial expression containers, such as instead of or in addition to facial actions derived from the video feed of the user.

For example, the device can implement vocal emotion recognition techniques to interpret an emotion in the user's voice and then verify that the facial actions detected in the concurrent sequence of video frames correspond to the same emotion.

5. Synthetic Face Generator

Similarly, the device and/or the remote computer system can implement a synthetic face generator to transform a facial landmark and expression container pair—representing a constellation of facial features of a user and an expression on the user's face in an image or frame—and a face model of the user into a synthetic face image that defines a photorealistic representation of the user's face with this same constellation of facial features and expression.

In particular, like the facial reconstruction model described above, the device and/or the remote computer system can inject a facial landmark and expression container pair—derived from an original image or frame of a user—and a face model of the user into the synthetic face generator to generate a synthetic face image that may be perceived as (at least) a superficially authentic photorealistic representation of the user's face in the same orientation, with the same distribution of facial features, and with the same facial expression as depicted in the original image or frame. For example, the device and/or the remote computer system can implement the synthetic face generator to generate a synthetic face image: to generate and validate a new face model for a user (e.g., during initial setup of the user's account); to generate and validate a new look model for the user; and/or to generate synthetic face images of another user during a video call.

Figure 3:
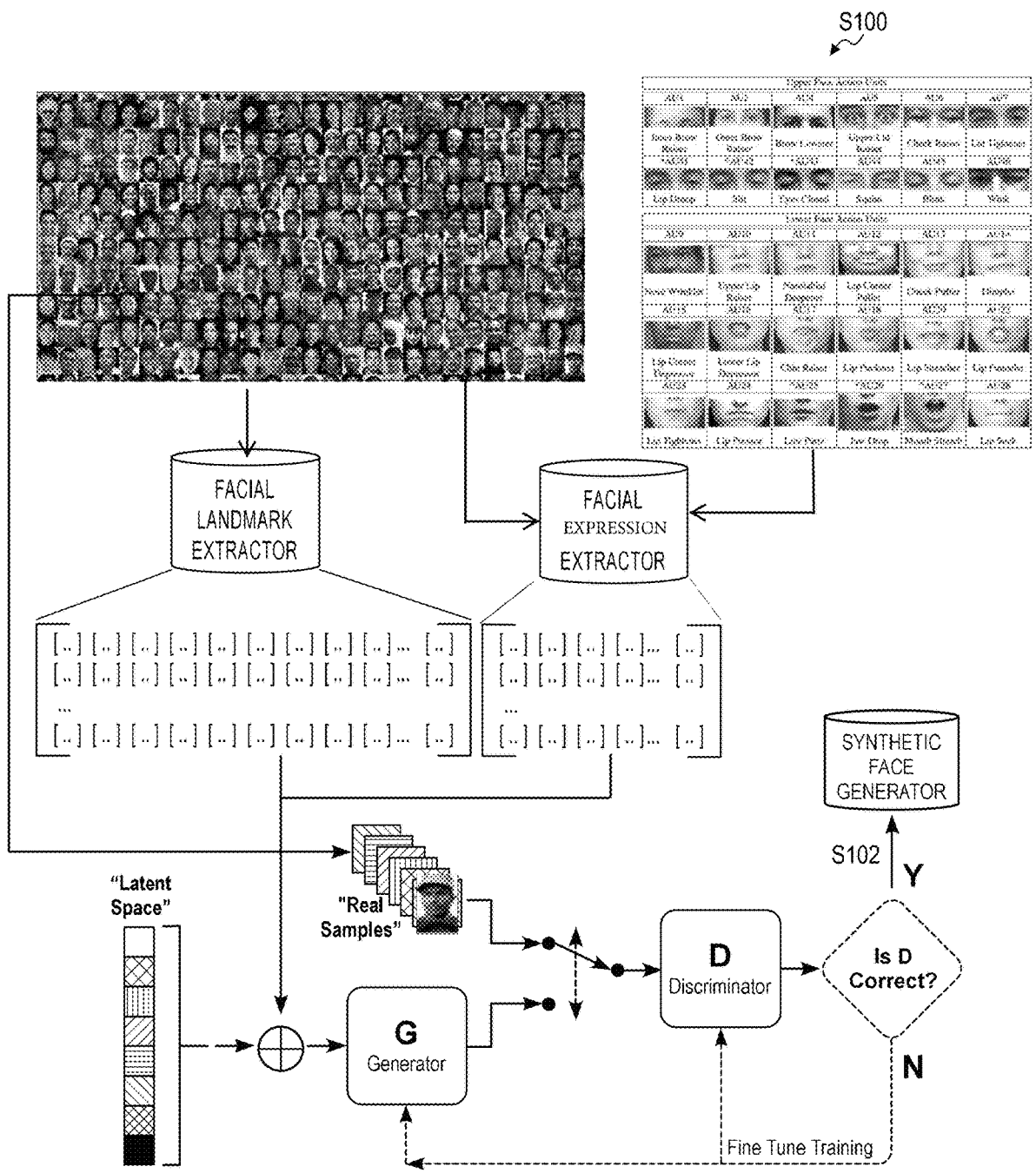
FIG. 3 is a flowchart representation of one variation of the method.

In one implementation shown in FIG. 3, in Block S102, the remote computer system: accesses a population of images of human faces (e.g., thousands, millions or 2D color images of human faces); implements the facial landmark extractor and the facial expression extractor to extract a facial landmark and expression container pair for each image in the population; and trains a conditional generative adversarial network to generate an image with statistics analogous to the population of images when supplied a facial landmark and expression container pair and a face model containing a set of coefficients or "weights," such as described below.

In particular, in Block S102, the remote computer system can train the conditional generative adversarial network to output a synthetic face image based on a set of input conditions, including: a facial landmark container, which captures relative locations (and/or sizes, orientations) of facial landmarks that represent a constellation of facial features across a human face; a facial expression container, which captures a facial expression of the human face; and a face model, which contains a (pseudo-) unique set of coefficients characterizing a unique human face and secondary physiognomic features (e.g., face shape, skin tone, facial hair, makeup, freckles, wrinkles, eye color, hair color, hair style, and/or jewelry). Therefore, the remote computer system (and local devices) can input values from a facial landmark and expression container pair and coefficients from a face model into the conditional generative adversarial network to generate a synthetic face image that depicts a face—(uniquely) represented by coefficients in the face model—exhibiting a facial expression, a mouth shape, an eye position, facial muscle actions, and/or a position of a face represented by the facial landmark and expression container pair.

The remote computer system can then store this conditional generative adversarial network as a synthetic face generator in Block S102 and distribute copies of this synthetic face generator to devices executing the application, as shown in FIG. 3.

6. Face Model Generation

Furthermore, the device can leverage the facial landmark extractor, the facial expression extractor, and the synthetic face generator to generate a face model for a user in Block S104, such as: based on a video clip captured by the device during a user account setup period; based on a video clip captured by the device just before (e.g., seconds, minutes before) initiating a video call with another device; or based on an image uploaded or selected by the user before or during a video call with another device.

6.1 Single-Image Face Model Calculation

In one implementation, the device (or the remote computer system): accesses a target image of the user; detects a face in a target region of the target image; implements the facial landmark extractor to generate a target facial landmark container; and implements the facial expression extractor to generate a target facial expression container. The device then: defines a target set of face model coefficients (or "weights," "conditions"); implements the synthetic face generator to transform the target facial landmark and expression container pair and the target set of face model coefficients into a target synthetic face image; and characterizes a first difference between the target synthetic face image and the target region of the target image depicting the face. The device further: adjusts the target set of face model coefficients to reduce the first difference; implements the synthetic face generator to transform the target facial landmark and expression container pair and the revised set of face model coefficients into a revised synthetic face image; characterizes a revised difference between the target synthetic face image and the revised region of the target image depicting the face; and repeats this process until this difference becomes asymptotic, approaches a null value, or falls below a threshold difference. Finally, the device generates a face model of the user based on the final set of face model coefficients thus calculated for the target image.

In this implementation, the user may upload or link to an existing image of herself, such as a digital copy of a headshot photograph or a profile image from a social networking website. Alternatively, the device can capture a photographic image of the user, such as during a user account setup period or just before (e.g., seconds, minutes before) a video call is started at the device. The device can then process this image locally to generate a face model for the user or upload this image to the remote computer system for remote face model generation.

In particular, the device (or the remote computer system) can: detect a face in a region of the image; extract or store this region of the image depicting the user's face as an "authentic face image"; implement the facial landmark extractor to extract a set of facial landmarks from the region of the image; and store these facial landmarks in a facial landmark and expression container pair. The device can then initialize a new face model for the user containing a set of baseline coefficients. For example, the device can: initialize set of baseline coefficients that represent an "average" face (e.g., [0.500, 0.500, 0.500, . . . , 0.500, 0.500]); or pseudo-randomly calculate baseline values for each coefficient in the new face model (e.g., [0.534, 0.023, 0.487, . . . , 0.324, 0.768]). The device injects baseline coefficients within the face model and the facial landmark and expression container pair into the synthetic face generator, which outputs a "baseline" synthetic face image and characterizes a baseline difference between the authentic face image and the baseline synthetic face image.

In one example, the device: compresses or upsamples the synthetic face image to match a resolution of the authentic face image; subtracts the baseline synthetic face image from the authentic face image in the green color space to calculate a deviation image in the green color space; calculates a green-space deviation value based on a combination (e.g., a sum) of absolute values contained in pixels in the green-space deviation image; repeats this process for the blue and red color spaces to calculate red- and blue-space deviation values; and quantifies a total difference between the authentic face image and the baseline synthetic face image based on a combination (e.g., a sum, an average) of the red-, green-, and blue-space deviation values.

In another example, the device implements a structural similarity index (or "SSIM") to quantify a baseline difference between the baseline synthetic face image and the authentic face image. In yet another example, the device: implements a facial recognition system to calculate a confidence that the face depicted in the synthetic face image is identical to the face depicted in the authentic face image; and characterizes a baseline difference between the synthetic face image and the authentic face image based on (e.g., inversely proportional to) this confidence.

Then, if the baseline difference exceeds a threshold (e.g., if a combination of red-, green-, and blue-space deviation values exceeds a threshold value; if a structural similarity index value for the baseline synthetic face image exceeds a threshold), then the device (or the remote computer system) can repeat the foregoing process to refine and validate coefficients in the face model.

For example, the device can implement reverse propagation techniques to adjust (or "perturb") a first coefficient in the face model in a first direction and repeat the foregoing process to generate a revised synthetic face image based on this revised face model and the facial landmark and expression container pair. Then, if a revised difference between the authentic face image and this revised synthetic face image is less than the baseline difference, the device can further perturb the first coefficient in the face model in the first direction. Conversely, if this revised difference between the authentic face image and the regenerated synthetic face image is greater than the baseline difference, the device can perturb the first coefficient in the face model in the opposite direction.

The device can repeat the foregoing process to refine the first coefficient in the face model, generate a new synthetic face image according to this revised face model, and verify that this new synthetic face image represents a better approximation of (i.e., exhibits less deviation from) the authentic face image than a synthetic face image generated according to a previous revision of the face model. The device can thus converge on a value for the first coefficient that minimizes a difference between: the authentic face image; and a synthetic face image generated by the synthetic face generator given the facial landmark and expression container pair.

The device can repeat this process for each other coefficient in the face model in order to converge on a set of coefficients that minimize a difference between: the authentic face image; and a synthetic face image generated by the synthetic face generator given the facial landmark and expression container pair. The device can also: store this set of coefficients in an initial face model; and then again repeat the foregoing process to further refine (or "tune") these coefficients, starting with this set of coefficients in the initial face model rather than baseline (e.g., average or pseudo-randomly-generated) coefficients described above.

(In one variation, the device can implement the foregoing methods and techniques to tune multiple coefficients in the face model concurrently rather than tune coefficients in the face model individually.)

Once a difference between the authentic face image and a synthetic face image generated according to this set of coefficients becomes asymptotic, approaches a null value, or falls below a threshold difference, etc., the device (or the remote computer system) can store this set of coefficients in a face model and associate this face model with the user.

The device can therefore iteratively refine a set of coefficients in order to generate a face model that—when injected into the synthetic face generator with the facial landmark and expression container pair—produces a synthetic face image that approximates the authentic face image, such as to a degree that a human may recognize the user in the synthetic face image and/or such that a human may discern no or limited visual differences between the authentic face image and the synthetic face image. More specifically, the device can execute the foregoing process to tune coefficients within a face model for the user such that insertion of this face model and the facial landmark and expression container pair—extracted from the authentic face image—into the synthetic face generator produces a realistic approximation of the facial expression, face shape, skin tone, facial hair, makeup, freckles, wrinkles, eye color, hair color, hair style, and/or jewelry, etc. depicted in the authentic face image. Furthermore, insertion of this face model and a different facial landmark and expression container pair—such as extracted from a video frame captured by the device during a later video call—into the synthetic face generator produces a realistic approximation of: the face shape, skin tone, facial hair, makeup, freckles, wrinkles, eye color, hair color, hair style, and/or jewelry, etc. depicted in the authentic face image; and the facial expression (e.g., a constellation of individual facial muscle and facial muscle group and actions) depicted in the video frame.

6.2 Face Model Calculation with Multiple Images

In a similar implementation shown in FIG. 4, the device (or the remote computer system) accesses a video clip of the user (e.g., captured by the device during a user account setup period, during a video call setup period preceding a video call with another user).

For each frame in a (sub)set of frames in the video clip, the device implements methods and techniques described above to: detect the user's face in a region of the frame; characterize positions of a set of features—analogous to facial landmark types in the predefined set of facial landmark types—in the region of the frame; represent positions of the set of features in a facial landmark and expression container pair; initialize a set of face model coefficients; insert the facial landmark and expression container pair and the set of face model coefficients into the synthetic face generator to generate a synthetic face image; characterize a difference between the synthetic face image and the region of the frame depicting the face; and iteratively adjust the set of face model coefficients to reduce a difference between the region of the frame and a synthetic face image generated according to these face model coefficients. The device then calculates a combination of these sets of face model coefficients associated with this (sub)set of frames and stores this combination as a face model for the user in Block S104.

In this implementation, the user may upload an existing video clip of herself, such as a video clip between five seconds and one minute in duration and/or containing between ten and 1,000 frames. Alternatively, the device can capture a video clip of the user, such as when a video call function is selected by the user and before a video call is initiated at the device. The device can then process this video clip locally to generate a face model for the user or upload this video clip to the remote computer system for remote face model generation.

6.2.1 Frame Selection

In particular, the device (or the remote computer system) can extract a set of frames from the video clip and then execute the foregoing methods and techniques to converge on a set of coefficients for each frame in this set. For example, the device can: implement methods and techniques described above to detect the user's face in each frame in the video clip; implement the facial landmark extractor to generate a facial landmark container for each frame in the video clip; implement the facial expression extractor to generate a facial expression container for each frame in the video clip; and select a subset of frames (e.g., ten frames, 32 frames, 64 frames)—from the video clip—that correspond to facial landmark and expression container pairs exhibiting least similarity and/or greatest ranges of facial landmark values within this set of facial landmark and expression container pairs. More specifically, the device can compare facial landmark and expression container pairs extracted from frames in the video clip to identify a subset of frames that represent a greatest range of face poses and facial expressions within the video clip.

In one variation, during the account setup period, the device can: retrieve a prerecorded video, sequence of images or memes, or audio configured to elicit a variety of emotions in a viewer, such as "neutrality," "happiness," "excitement," "sadness," "confusion," "surprise," "anger," "fear," and/or "contempt." The device can then replay this prerecorded video, sequence of images or memes, or audio for the user—thereby triggering the user to express a range of authentic emotions—while capturing the video clip of the user. The device can then: insert frames from this video clip into the facial landmark extractor to generate a feed of facial landmark containers; insert frames from this video clip into the facial expression extractor to generate a feed of facial expression containers; and isolate a subset of facial landmark and expression container pairs that contain combinations of action units that correspond (with greatest similarity) to emotions described by the prerecorded video, sequence of images or memes, or audio. For example, the device can identify one facial landmark and expression container pair for each of "neutrality," "happiness," "excitement," "sadness," "confusion," "surprise," "anger," "fear," and/or "contempt."

The device can then allocate this subset of facial landmark and expression container pairs for construction of the face model for the user.

6.2.2 First Frame

The device can then: select a first frame—from this subset of frames—associated with a first facial landmark and expression container pair; extract a first authentic face image from a region of the first frame depicting the user's face; initialize a set of baseline coefficients, as described above; and execute the processes described above to perturb these baseline coefficients and to converge on a first set of coefficients that—when combined with the first facial landmark and expression container pair—produces a synthetic face image exhibiting a minimum difference from the first authentic face image.

6.2.3 Sensitivity

The device can also characterize a sensitivity of each coefficient—in this first set of coefficients—to accurate reproduction of the first authentic face image.

For example, once the device converges on a final value of a first coefficient in this first set of coefficients, the device can: pass the first set of coefficients—including the final value of the first coefficient—and the first facial landmark and expression container pair into the synthetic face generator to generate a first synthetic face image; quantify a first difference between the first synthetic face image and the first authentic face image; perturb the final value of the first coefficient—in the first set of coefficients—by a perturbation unit (e.g., "0.005"); pass this perturbed set of coefficients—including the perturbed value of the first coefficient—and the first facial landmark and expression container pair into the synthetic face generator to generate a perturbed synthetic face image; quantify a perturbed difference between the perturbed synthetic face image and the first authentic face image; and calculate a sensitivity of the first coefficient for the first frame proportional to a magnitude of difference between the first difference and the perturbed difference.

More specially, if perturbation of the final value of the first coefficient by the perturbation unit produces a small deviation from maximum (or "best") correspondence between a synthetic face image and the first authentic face image, the device can calculate a low sensitivity of the first coefficient for the first frame. However, if perturbation of the final value of the first coefficient by the perturbation unit produces a large deviation from maximum (or "best") correspondence between a synthetic face image and the first authentic face image, the device can calculate a high sensitivity of the first coefficient for the first frame.

The device can repeat this process for each other coefficient in the first set of coefficients to characterize sensitivity of accurate reproduction of the first authentic face image to each coefficient in this first set of coefficients.

6.2.4 Additional Frames

The device can repeat the foregoing process for each other frame in the (sub)set of frames, including: calculating a set of coefficients that minimize a difference between an authentic face image extracted from a frame and a synthetic face image generated according to the set of coefficients and a facial landmark and expression container pair extracted from the frame image; and characterizing sensitivity of accurate reproduction of the authentic face image to each coefficient in the set of coefficients for each frame in the (sub)set of frames.

More specifically, the device can repeat the foregoing process for each other frame in the (sub)set of frames in order to generate a population of coefficient sets, wherein each set of coefficients in the population is tuned for one corresponding frame in the (sub)set of frames and wherein each coefficient in each set of coefficients in the population is associated with a sensitivity.

6.2.5 Face Model Composition

The device can then combine corresponding coefficients across this population of coefficient sets to calculate a face model for the user.

For example, the device can: calculate a first linear combination of first coefficients—across this population of coefficient sets—weighted by their corresponding sensitivities; store this first linear combination as a first composite coefficient; calculate a second linear combination of second coefficients—across this population of coefficient sets—weighted by their corresponding sensitivities; store this second linear combination as a second composite coefficient; and repeat this process for each other coefficient in this population of coefficient sets. The device then aggregates these composite coefficients into a face model for the user Therefore, the device can execute the foregoing process to tune coefficients within sets of coefficients for individual frames depicting the user and then fuse these sets of coefficients into one face model for the user. Insertion of this face model and a first facial landmark and expression container pair—extracted from a first frame in this set—into the synthetic face generator produces a first realistic approximation of the facial expression, face shape, skin tone, facial hair, makeup, freckles, wrinkles, eye color, hair color, hair style, and/or jewelry, etc. depicted in the first frame. Similarly, insertion of this face model and a second facial landmark and expression container pair—extracted from a second frame in this set—into the synthetic face generator produces a second realistic approximation of the facial expression, face shape, skin tone, facial hair, makeup, freckles, wrinkles, eye color, hair color, hair style, and/or jewelry, etc. depicted in the second frame.

Furthermore, insertion of this face model and a different facial landmark and expression container pair—such as extracted from a video frame captured by the device during a later video call—into the synthetic face generator produces a realistic approximation of: the face shape, skin tone, facial hair, makeup, freckles, wrinkles, eye color, hair color, hair style, and/or jewelry, etc. depicted in the set of frames; and the facial expression depicted in the video frame.

6.3 Look Model

In one variation, the device (or the remote computer system) executes the foregoing processes: to calculate a set of face model coefficients for a "look" image uploaded or selected by the user (e.g., a digital photograph representing a physiognomy preferred by the user); to calculate a population of face model coefficient sets for frames in a video clip of the user; and to fuse these face model coefficient sets into a "look" model for the user, which yields synthetic face images that appear as the face in the "look" image when inserted into the synthetic face generator but that exhibit greater robustness to changes in relative positions of facial features and facial expression than a face model generated from a single frame or image.

For example, the device can execute the process described above to: extract a target authentic face image from the look image; extract a target facial landmark and expression container pair from the target authentic face image; converge on a target set of coefficients that minimize a difference between the target authentic face image and a synthetic face image generated by the synthetic face generator given the facial landmark and expression container pair; and characterize sensitivity of accurate reproduction of the target authentic face image to each coefficient in the target set of coefficients.

The device can then combine this target set of coefficients with the face model—generated according to a (sub)set of frames extracted from a video clip—to generate a look model for the user. For example, the device can: retrieve a population of coefficient sets generated for the user based on the (sub)set of frames; retrieve a sensitivity for each coefficient in each coefficient set in this population; assign a target weight (e.g., 0.900) to each coefficient in the target set of coefficients generated according to the look image; and assign a secondary weight—less than the target weight (e.g., 0.100)—to each coefficient set in the population of coefficient sets. For a first coefficient, the device can then: calculate a corrected weight of the first coefficient in the target set of coefficients based on a combination (e.g., a product) of the target weight and a sensitivity of the first coefficient in the target set of coefficients; calculate corrected weights of the first coefficient across the population of coefficient sets based on combinations (e.g., products) of the secondary weight and sensitivities of the first coefficient across the population of coefficient sets; calculate a first linear combination of first coefficients—across the target coefficient set and the population of coefficient sets—according to their corresponding corrected weights; and store this first linear combination as a first composite coefficient in the look model. Similarly, for a second coefficient, the device can: calculate a corrected weight of the second coefficient in the target set of coefficients based on a combination of the target weight and a sensitivity of the second coefficient in the target set of coefficients; calculate corrected weights of the second coefficient across the population of coefficient sets based on combinations of the secondary weight and sensitivities of the second coefficient across the population of coefficient sets; calculate a second linear combination of second coefficients—across the target coefficient set and the population of coefficient sets—according to their corresponding corrected weights; and store this second linear combination as a second composite coefficient in the look model. The device can repeat this process for each other coefficient in this target set of coefficients and the population of coefficient sets in order to complete this look model for the user.

Therefore, the device can execute the foregoing process to tune coefficients in the face model according to a look image provided by the user and to compile these tuned coefficients into a look model. Insertion of this look model and a first facial landmark and expression container pair—extracted from a look image—into the synthetic face generator produces a realistic approximation of the facial expression, face shape, skin tone, facial hair, makeup, freckles, wrinkles, eye color, hair color, hair style, and/or jewelry, etc. depicted in the look image.

Furthermore, insertion of this look model and a different facial landmark and expression container pair—such as extracted from a video frame captured by the device during a later video call—into the synthetic face generator produces a realistic approximation of: the face shape, skin tone, facial hair, makeup, freckles, wrinkles, eye color, hair color, hair style, and/or jewelry, etc. depicted in the look image; and the facial expression depicted in the video frame.

More specifically, in this variation, the device can leverage the face model (or a population of coefficient sets) generated for the user in order to create a "look model" based on a single look image. When the look model is injected into the synthetic face generator, the synthetic face generator can thus return a synthetic face image that approximates: the skin tone, facial hair, makeup, hair style, and/or jewelry, etc. depicted in the look image; rather than the skin tone, facial hair, makeup, hair style, and/or jewelry, etc. depicted in the set of images that yielded the face model. In particular, synthetic face images generated by the synthetic face generator according to the look model may thus resemble the user's face in the look image rather than the user's face in the set of frames.

The device can thus generate a new look model for the user based on a single look image provided by the user, such as a personal favorite candid photo of the user from an event for which a video or multiple images of the user are not available.

6.4 Multiple Looks

Figure 2A:
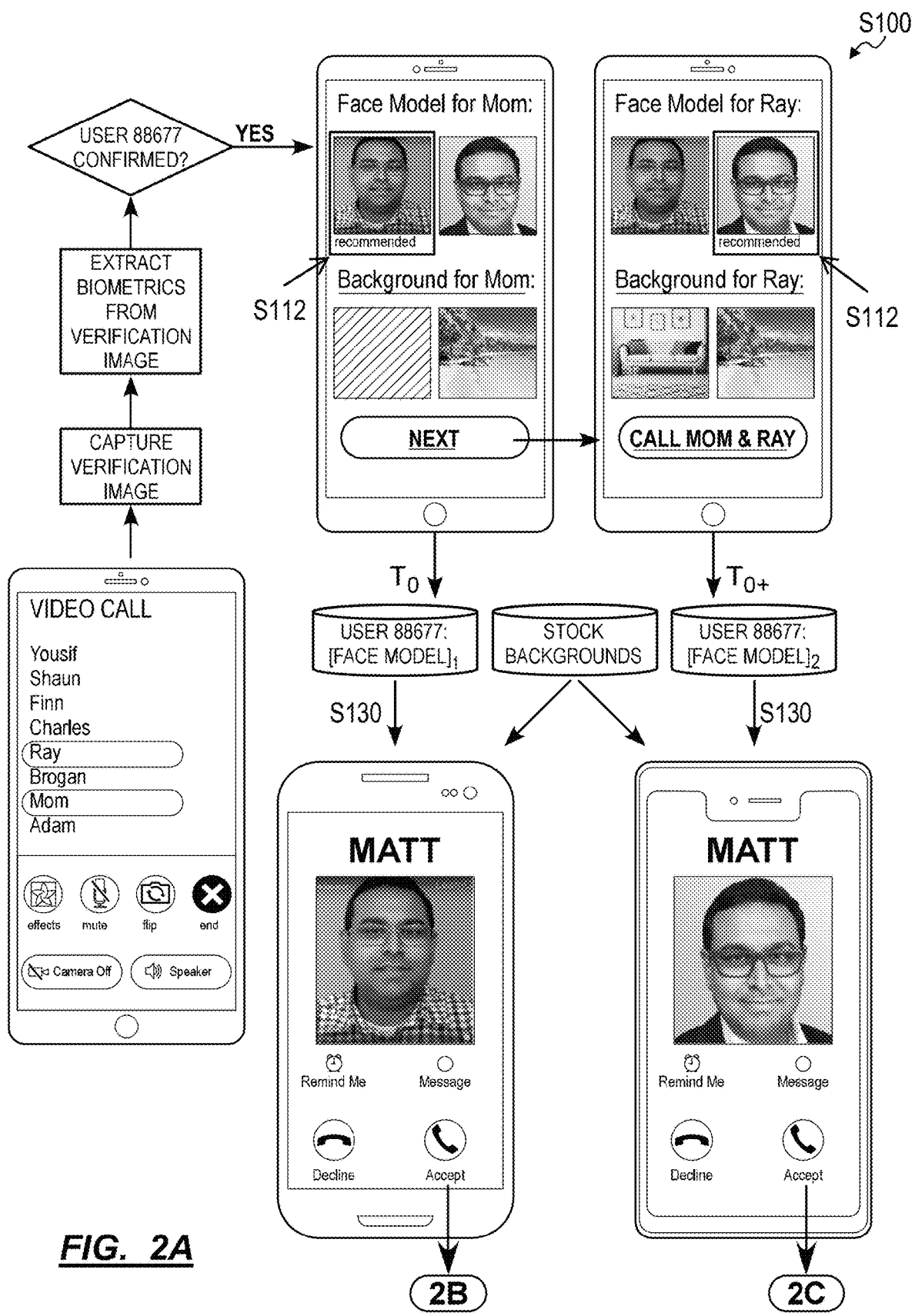
FIGS. 2A-2D are flowchart representations of one variation of the method.

The device (or the remote computer system) can execute the foregoing methods and techniques to generate a face model and a set of look models for the user and to associate this face model and these look models with the user, such as by storing this face model and these look models in the user's account, as shown in FIGS. 1 and 2A.

In one variation, the device also prompts the user to associate each look model with a particular contact or group of contacts. For example, the device can execute the foregoing process to generate: a first look model based on a first look image depicting the user as clean-shaven, clean-cut, without a hat, and wearing a tie; a second look model based on a third look image depicting the user as clean-shaven, clean-cut, without a hat, and without a tie; a third look model based on a third look image depicting the user with a beard and wearing a hat; and a fourth look model based on a fourth look image depicting the user with a beard, longer hair, and wearing facial piercings. In this example, the device can interface with the user: to associate the first look model with a first group of work-related contacts; to associate the second look model with a second group of contacts including the user's grandparents and extended family; to associate the third look model with a third group of contacts including the user's parents and siblings; and to associate the fourth look model with a fourth group of contacts including the user's closet friends, spouse, and children.

However, the device (and/or the remote computer system) can generate a set of face and look models and associate these face and look models within individual contacts or groups of contacts in any other way.

6.5 Security

When generating a face model based on an image or video clip of the user, the device (or the remote computer system) extracts biometric data (e.g., a "faceprint") from the image or video clip and associates these biometric data with the face model. Later, the device enables a second device to access this face model of the user during a video call only after positively matching biometric data extracted from a video frame captured by the device during this video call to biometric data associated with the face model, such as described below.

Additionally or alternatively, when the user supplies a look image for generation of a look model, the device (or the remote computer system) can: extract biometric data from the look image; verify correspondence between these biometric data and biometric data associated with the existing face model; and then generate a look model based on the look image and the existing face model only after confirming correspondence between these biometric data. Similarly, the device can verify correspondence between biometric data extracted from a look image and a video clip captured by the device before transforming the look image and this video clip into a look model, as described above.

7. Body Model

Figure 2B:
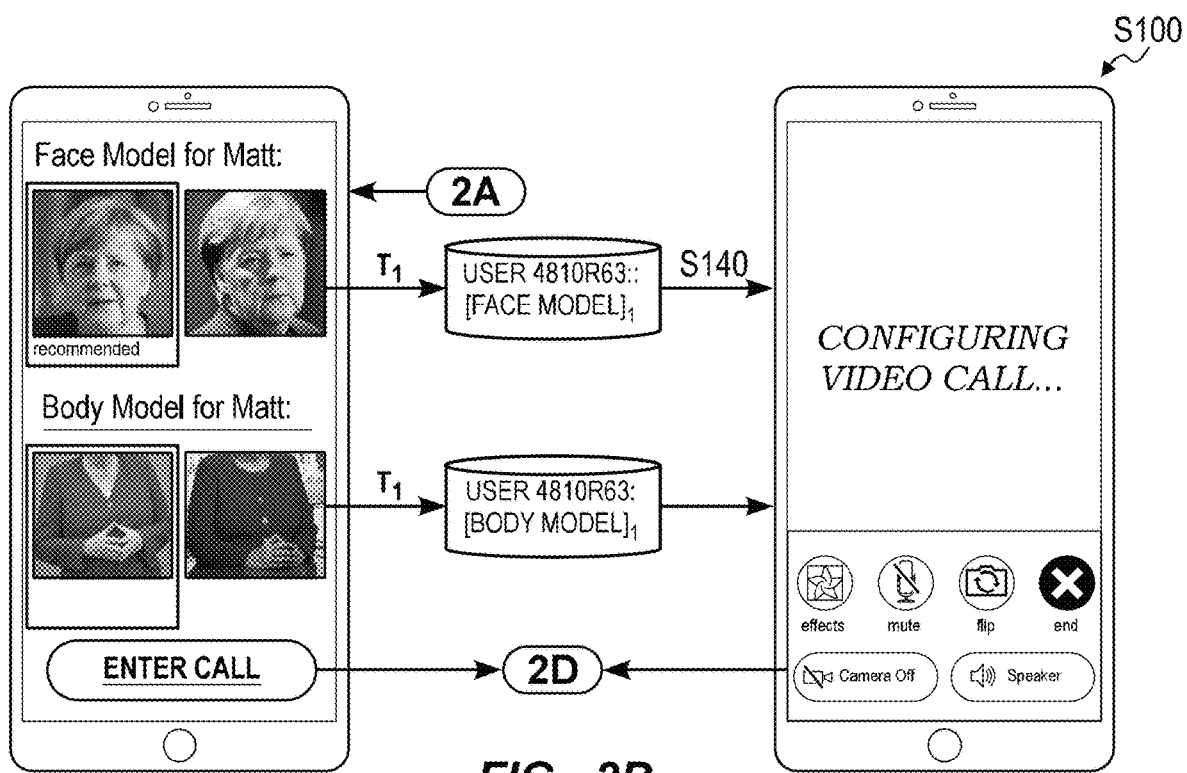

In one variation shown in FIG. 2B, the device (and/or the remote computer system) implements similar methods and techniques to generate a body model for the user.

In this variation, the device (and/or the remote computer system) can implement a body landmark extractor to detect a body in a region of an image (e.g., a photographic image, a frame in a video clip, and/or a frame in a live video feed); to scan this region of the image for features analogous to predefined body landmark types; and to represent location, orientations, and/or sizes, etc. of these analogous features—detected in the region of the image—in one body landmark container. In particular, the device and/or the remote computer system can implement the body landmark extractor: to detect spatial characteristics of a body—such as including positions of a neck, shoulders, a chest, arms, hands, an abdomen, a waist—depicted in a 2D image; and to represent these spatial characteristics in a single container (e.g., a vector, a matrix).

Furthermore, the device (and/or the remote computer system) can similarly: implement a body language extractor (e.g., similar to the facial expression extractor) to extract a set of body action units representing torso and extremity motions indicative of the user's emotions (e.g., "body language"); and to compile these body action units into a body language container. (Additionally or alternatively, the device can verify that the facial actions detected in the concurrent video frame correspond to the same emotion indicated by the set of body action units detected in this image.)

Similarly, the device and/or the remote computer system can implement a synthetic body generator to transform a body landmark container and a body language container—representing a posture and torso and extremity action units of a user detected in an image or frame—and a body model of the user into a synthetic body image, which defines a photorealistic representation of the user's body (e.g., torso, arms) with this same posture and exhibiting the same body language. In particular, like the facial reconstruction model and synthetic face generator described above, the device and/or the remote computer system can inject a body landmark container—derived from an original image or frame of a user—and a body model of the user into the synthetic body generator to generate a synthetic body image that may be perceived as (at least) a superficially authentic photorealistic representation of the user's body with the same posture depicted in the original image or frame.

Thus, in this variation, the device (or the remote computer system) can implement methods and techniques similar to those described above to access an individual image, a set of images, and/or a look image of the user. For each image in this set, the device can: detect a body (e.g., neck, shoulders, chest, arms, hands, abdomen, waist) in a region of the image; extract an authentic body image from this region of the image; implement the body landmark extractor to extract a body landmark container from the image; and calculate a set of coefficients that—when injected into the synthetic body generator with the body landmark container—produces a synthetic body image that approximates the authentic body image, such as to a degree that a human may recognize the user's body in the synthetic body image and/or such that a human may discern limited visual differences between the authentic body image and the synthetic body image. The device can then fuse this population of coefficient sets into a body model for the user and store this body model in association with the user, such as linked to the user's account.

The device (or the remote computer system) can also generate multiple body models for the user—such as based on multiple look images depicting the user wearing different garments (e.g., a suit, business casual dress, athletic wear, pajamas)—and link these body models to the user's account. The device can additionally or alternatively link each body model of the user to a correct face or look model generated according to the same image or video clip.

7.1 Body Component Model

Additionally or alternatively, rather than generate and manipulate a single body model that represents the user's neck, shoulders, chest, arms, hands, abdomen, and/or waist, etc., the device (and/or the remote computer system) can instead implement similar methods and techniques to generate individual body component models for the user's torso, extremities, and/or other body parts, such as including: a neck model; a chest model; a back model; a left arm model;

a right arm model; a left hand model; a right hand model; an abdomen model; a waist model; a left thigh model; a right thigh model; a left shin model; a right shin model; a left foot model; and/or a right foot model.

8. Preemptive Model Generation

Generally, the device (and/or the remote computer system) can interface with the user as described above to generate a face model, a set of looks models, and/or a set of body models for the user prior to a video call, such as when a user creates a user account within the application or just prior to (e.g., seconds, minutes before) entering a video call with another user, as shown in FIG. 4. Later, in preparation for a video call, the device can: preset a list of face and/or look models associated with the user's account to the user; receive a selection of a particular face or look model—in this set of face and look models—from the user in Block S112; and load a local copy of the particular face or look model or trigger other devices connected to this video call to download local copies of the particular face or look model, as described below.

9. Video Call Configuration

When a first user opens the native or browser-based video conferencing application executing on a first device, the first device can interface with the user to configure an upcoming video call with a second user, including selection of a face model, look model, body model, and/or background for representing the first user at the second user's device, as shown in FIGS. 2A and 2B.

9.1 Biometric Check

In one implementation shown in FIG. 2A, just before or at the start of the video call, the first device: captures a verification image or a verification video clip of the first user; extracts biometric data from the verification image or verification video clip; and confirms that these extracted biometric data match or sufficiently correspond to biometric data associated with the user's account.

9.2 Face/Look Model Selection

Upon confirming this correspondence, the first device can prompt the user to select from a set of available face and look models—associated with the user—for the upcoming video call.

For example, after confirming the identify of the first user based on biometric data extracted from the verification image or verification video clip, the first device can access or generate a synthetic face image for each available face and look model linked to the user's account, such as by injecting a nominal facial landmark and expression container pair (e.g., representing a face with a neutral expression (or action unit "0")) and each available face and look model into the synthetic face generator to generate a set of nominal synthetic face images representing this set of face and look models. The first device can then render these synthetic face images within the application and prompt the first user to select a synthetic face image from this set, as shown in FIGS. 2A and 2B.

In this example, the first device can also suggest or recommend a particular face or look model for the video call. For example, if the first user has elected the second user from a contact list or address book and previously associated face and look models in her account with different groups of contacts, the first device can recommend a particular face or look model—from this set of available face and look models—associated with a contact group including the second user.

The first device can then retrieve a face or look model thus selected by the user (e.g., from local memory or from a remote database) and transmit a copy of this face or look model to the second user's device, as shown in FIGS. 2A and 2B. Alternatively, the first device can return this selection to the remote computer system, and the remote computer system can transmit a copy of the corresponding face or look model to the second user's device. Accordingly, the second device can load and store a temporary copy of this face model of the first user for the duration of this video call.

9.3 Failed Biometric Check

Conversely, if the first device fails to verify that biometric data extracted from the verification image or verification video clip match or sufficiently correspond to biometric data associated with the first user's account, the first device (and/or the remote computer system) can: disable transmission of a facial landmark and expression container feeds from the first device to the second device; and implement methods and techniques described below to generate a new face model or new look model for the first user in (near) real-time based on a video clip captured by the user's device just before or just after the first user enters the video call.

Once the first device (or the remote computer system) generates this new face or look model for the first user, the first device (or the remote computer system) can: transmit this new face or look model to the second device; and activate transmission of a facial landmark and expression container feeds from the first device to the second device.

Alternatively, if the first device fails to verify that biometric data extracted from this verification image or verification video clip match or sufficiently correspond to biometric data associated with the user's account, the first device (and/or the remote computer system) can query a corpus of face and look models stored in a remote database for a subset of face and/or look models associated with biometric data that match or sufficiently correspond to biometric data extracted from the verification image or verification video clip. Upon identifying this subset of face and/or look models, the first device can implement methods and techniques similar to those described above to: present these face and/or look models to the first user, such as by rendering synthetic face images generated according to these face and/or look models; prompt the first user to select from this subset of face and/or look models; and then queue transmission of the selected face or look model to the second device.

9.4 Body Model

In one variation in which the first device (or the remote computer system) previously generated a body model of the first user and linked this body model to the first user's account, the first device can also queue transmission of this body model to the second device, such as after verifying an identity of the first user.

Alternatively, in this variation, if the user's account contains multiple body models and multiple face or look models, the first device can select a particular body model linked to the face or look model selected by the user for this video call and queue transmission of this body model to the second device. Yet alternatively, if the user's account contains multiple body models, then the first device can: prompt the user to select from this set of body models, such as by rendering synthetic body images generated according to these available body models; and then queuing transmission of a body model—thus selected by the first user—to the second device, as shown in FIG. 2B.

9.5 Background Selection

In one variation, the first device also prompts the first user to elect a background for the video call.

For example, the first device can access a corpus of preexisting static and dynamic (e.g., animated) backgrounds, such as including: solid background colors (e.g., white, gray, yellow); background patterns (e.g., a television test pattern, a brocade pattern, a chevron patter); a stock image (e.g., a stock conference room image, a stock outdoor image, a stock beach image); and/or a stock video clip (e.g., a stock video clip of a beach with waves crashing in a background). In this example, the first device prompts the first user to select from this corpus of preexisting static and dynamic (e.g., animated) backgrounds for the video call, as shown in FIGS. 2A and 2B.

In this example, the first device can also enable the user to upload a background image, such as a photographic image of the user's office, living room, or favorite space. Additionally or alternatively, the first device can extract a background from a look image previously provided by the user or from the verification image or verification video clip captured before the start of the video call and enable the user to select this background for the duration of the video call.

Upon selection of the background by the first user, the first device can transmit a copy of the background to the second device or otherwise queue the second device to load this background.

9.6 Second Device

Therefore, prior to initiating a video call with the second device, the first device can interface with the first user to select a face or look model of the first user, a body model of the first user, and/or a background for her synthetic video feed, which together define how the first user is visually presented to the second user during the video call. Prior to entering or at the start of the video call, the second device can access or download local copies of the selected face or look model of the first user (hereinafter the "first face model"), the selected body model of the first user (hereinafter the "first body model"), and/or the background selected by the first user (hereinafter the "first background"), as shown in FIG. 2A. More specifically, prior to the video call, the first device (or the remote computer system) can automatically grant the second device permission to securely download the first face model, etc. selected by the first user.

Concurrently and prior to entering the video call, the second device can interface with the second user to select a face or look model of the second user, a body model of the second user, and/or a background for her synthetic video feed during the video call, which together define how the second user is visually presented to the first user during the video call, as shown in FIG. 2B. Prior to entering or at the start of the video call, the first device can access or download local copies of the selected face or look model of the second user (hereinafter the "second face model"), the selected body model of the second user (hereinafter the "second body model"), and/or the background selected by the second user (hereinafter the "second background"). More specifically, prior to the video call, the second device (or the remote computer system) can automatically grant the first device permission to securely download the first face model, etc. selected by the second user.

10. Variation: Real-time Face Model/Look Model Generation

Figure 2C:
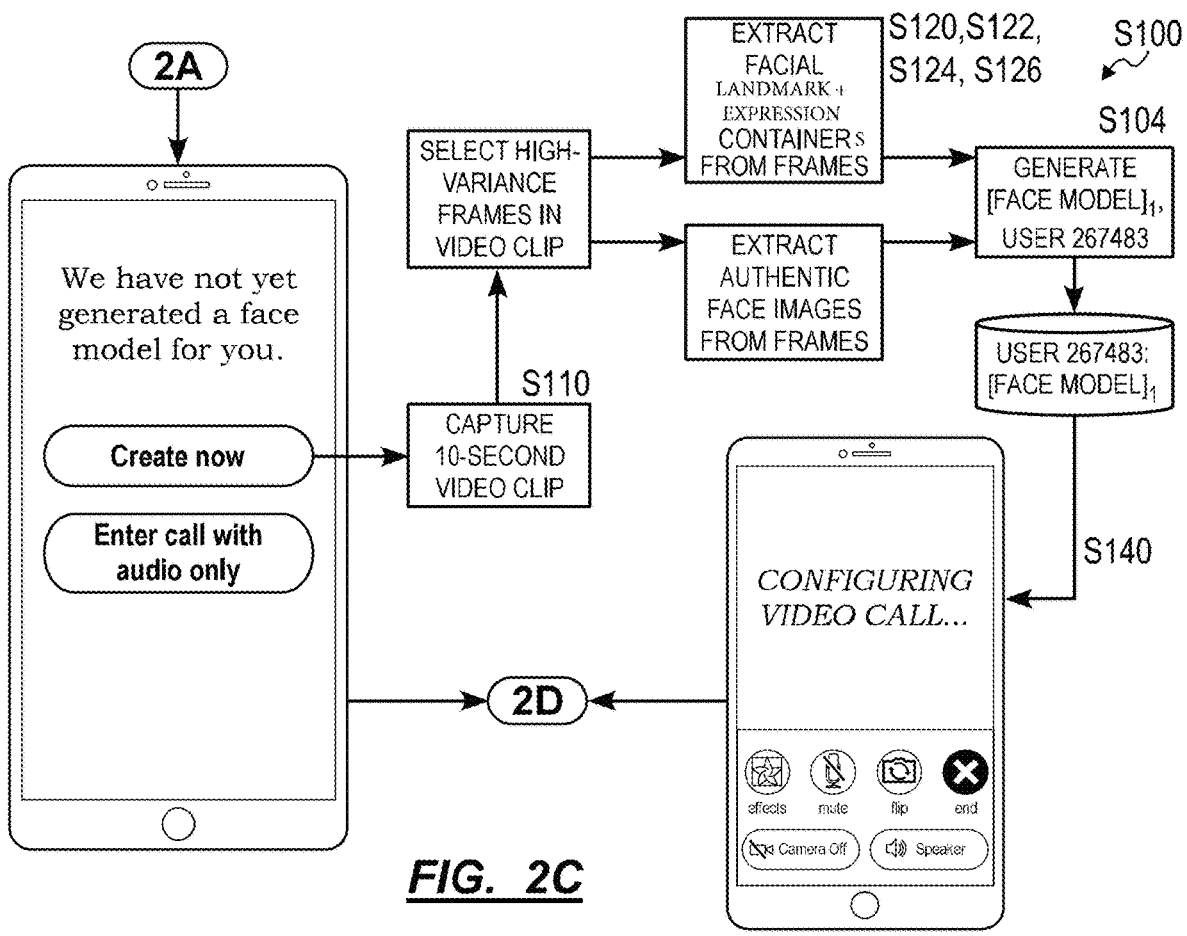

In one variation shown in FIG. 2C, if a face model of the first user is not available upon selection of a video call with the second user (or if a look model that the first user prefers for this video call is not available), the first device (and/or the remote computer system) can: enable transmission of a first audio feed to the second device; disable transmission of facial landmark and expression container feeds to the second device (and therefore disable generation of a synthetic video feed of the first user at the second device); capture a video clip of the first user; (access a look image uploaded by the first user;) and implement methods and techniques described above to generate a new face model (or a new look model) for the first user based on the video clip (and the look image). Upon generating a new face model (or a new look model) for the first user, such as approximately one minute later, the first device can: return the new face model (or the new look model) to the second device; link the new face model (or the new look model) to the first user's account; and enable transmission of facial landmark and expression container feeds from the first device to the second device (and therefore enable generation of a synthetic video feed of the first user at the second device).

In this variation, the first device can also execute this process to generate a new face model (or a new look model) in real-time during the video clip when manually triggered by the first user. The first device can then queue the second device to download a copy of this new face model (or new look model) during the video call. Upon receipt of this new face model (or new look model), the second device can implement this new face model (or new look model)—rather than a second face model previously selected by the first user for this video call—to transform facial landmark and expression container pairs received from the first device into synthetic face images of the first user.

10.1 Real-Time Body Model Generation

In this variation, the first device can implement similar methods and techniques to generate a new body model for the user in (near) real-time based on a video clip captured by the first device at the start of the video call.

However, the first device can implement any other methods or techniques to configure an upcoming or current video call with a face model, body model, and/or background selected by the first user and to serve these data to the second device; and vice versa.

11. Video Call

Then, during the video call, the first device can: capture a first video feed in Block S110; implement a local copy of the facial landmark extractor to represent constellations of facial landmarks—detected in the first video feed—in a first feed of facial landmark containers in Block S122; implement a local copy of the facial expression extractor to represent facial muscle actions—detected in the first video feed—in a first feed of facial expression containers in Block S126; and transmit the first feed of facial landmark and expression container pairs to the second device in Block S130. Upon receipt, the second device can: insert the first feed of facial landmark and expression container pairs and a local copy of the first face model of the first user into a local copy of the synthetic face generator to generate a first feed of synthetic face images in Block S150; and render this first feed of synthetic face images over the first background in Block S152, shown in FIG. 2D.

Concurrently, the second device can: capture a second video feed in Block Silo; implement a local copy of the facial landmark extractor to represent constellations of facial landmarks—detected in the second video feed—in a second feed of facial landmark containers in Block S122; implement a local copy of the facial expression extractor to represent facial muscle actions—detected in the second video feed—in a second feed of facial expression containers in Block S126; and transmit the second feed of facial landmark and expression container pairs to the first device in Block S130. Upon receipt, the first device can: insert the second feed of facial landmark and expression container pairs and a local copy of the second face model of the second user into a local copy of the synthetic face generator to generate a second feed of synthetic face images in Block S150; and render the second feed of synthetic face images over the second background in Block S152, shown in FIG. 2D.

11.1 Facial Landmark and Expression Container Feeds

In particular, in preparation for the video call, the first device can: load local copies of the synthetic face generator, the facial landmark extractor, the facial expression extractor, the second face model of the second user, and the second background selected by the second user. During the video call, the first device can: capture a first audio feed; compress the first audio feed into a first feed of audio packets; capture a first video feed; compress the first video feed into first facial landmark and expression container feeds; and stream the first feed of audio packets and the first facial landmark and expression container feeds to the second device in near real-time (e.g., with a maximum time of 50 milliseconds from capture to upload).

For example, for a first video frame in the first video feed, the first device can implement the facial landmark extractor to: detect the first user's face in a first region of the first video frame; detect positions of facial landmarks in the first region of the first video frame; and generate a first facial landmark container that represents positions of these facial landmarks in the first region of the first video frame. The first device can concurrently implement the facial expression extractor to: detect muscle actions in the first region of the first video frame; generate a first facial expression container that represents presence and/or intensity of these detected muscle actions in the first region of the first video frame; and link this facial expression container with the corresponding facial landmark container, such as via a common timestamp or frame identifier. The first device can then upload the first facial landmark and expression container pair with a first audio packet—captured around (e.g., within 50 milliseconds of) a capture time of the first video frame—to a computer network, which distributes the first facial landmark and expression container pair and the first audio packet to the second device.

In one variation described above, the first device can also: implement vocal emotion recognition to interpret an emotion exhibited in speech by the first user captured in the first audio packet; verify accuracy of the facial muscle actions derived form the first video frame based on alignment of the expression predicted by these facial muscle actions with the speech-based emotion; and/or write the speech-based emotion to first facial expression container.

Then, for a second (e.g., next) video frame in the first video feed, the first device can: implement face tracking or object tracking techniques to track the first user's face from the first region in the first frame to a second region in the second video frame; and implement the facial landmark extractor to generate a second facial landmark container that represents positions of facial landmarks in the second region of the second video frame. The first device can concurrently implement the facial expression extractor to: detect muscle actions in the second region of the second video frame; generate a second facial expression container that represents presence and/or intensity of these detected muscle actions in the second region of the second video frame; and link this facial expression container with the corresponding facial landmark container, such as via a common timestamp or frame identifier. The first device can then upload the second facial landmark and expression container pair with a second audio packet—captured around a capture time of the second video frame—to the computer network, which distributes the second facial landmark and expression container pair and the second audio packet to the second device.

(The first device can also fuse a second speech-based emotion derived from the second audio packet with the second facial expression container, as described above.)

Concurrently, the second device can implement similar methods and techniques to stream a second feed of audio packets and a second facial landmark and expression container feeds to the first device.

11.2 Synthetic Face Image Feeds

During the video call, the second device renders the first background in a video call portal within a second instance of the application executing on the second device.

Upon receipt of a facial landmark and expression container pair and a corresponding audio packet from the first device, the second device can: extract audio data from the audio packet; insert the facial landmark and expression container pair and the first face model of the first user into a local copy of the synthetic face generator—stored in local memory on the second device—to generate a synthetic face image; and render the synthetic face image over the first background within the video call portal (e.g., to form a "first synthetic video feed") while playing back the audio data via an integrated or connected audio driver.

By repeating this process for each audio packet and facial landmark and expression container pair received from the first device during the video call, the second device can thus generate and render a first synthetic video feed depicting the first user's face over the first background—synchronized to playback of an audio stream from the first device—in near real-time (e.g., with less than one second of latency).

The first device can implement similar methods and techniques during the video call to generate and render a second synthetic video feed depicting the second user's face over the second background—synchronized to playback of an audio stream from the second device—in near real-time.

11.3 Variation: Synthetic Body Image Feeds

Figure 2D:
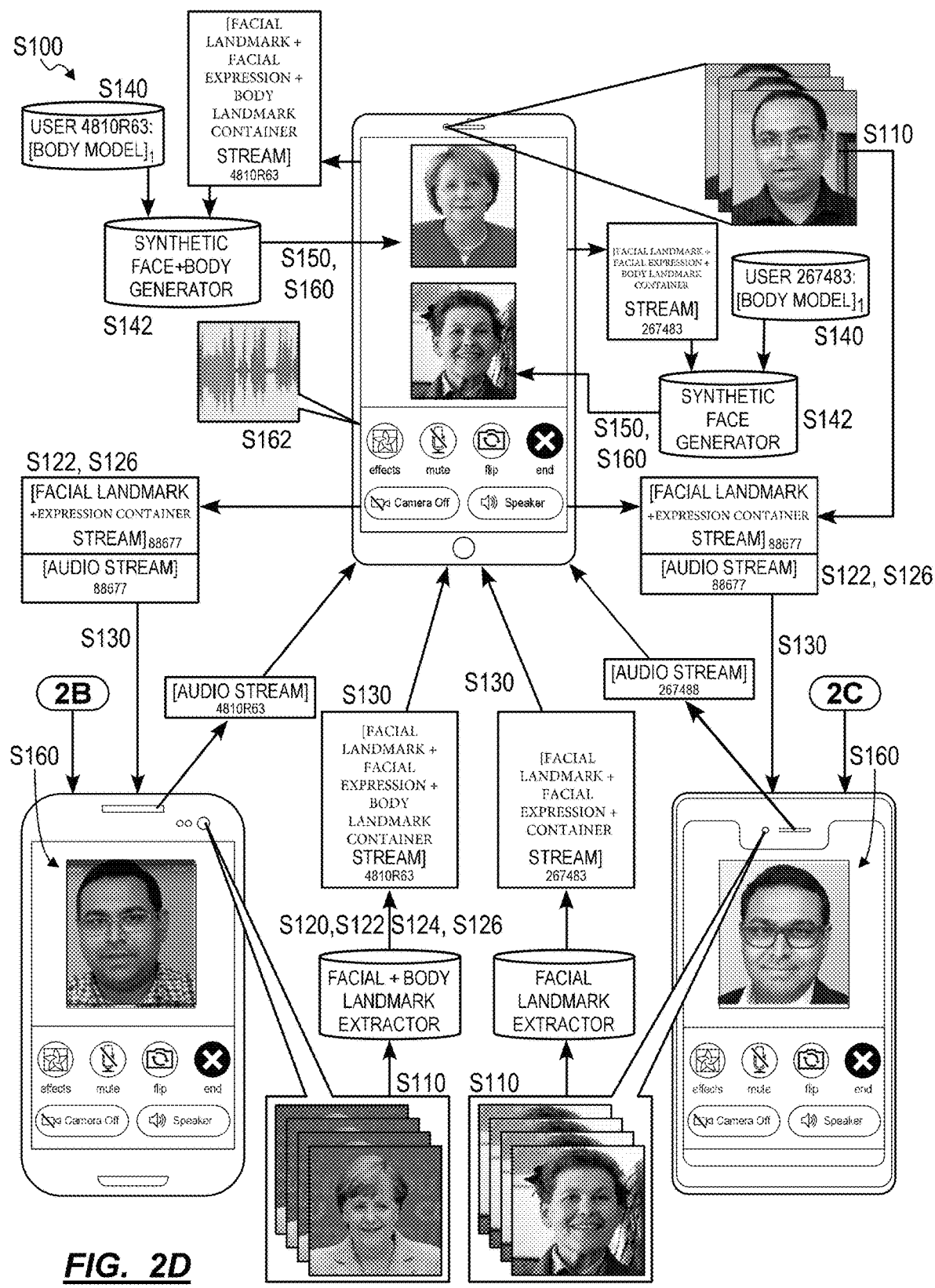

In one variation shown in FIG. 2D, the first device similarly: detects the first user's body in the first video feed; transforms the first video feed into a first feed of body landmark containers and/or body language containers; and streams this first feed of body landmark containers and/or body language containers to the second device. In this variation, the second device can then implement similar methods and techniques: to inject the first body model and each subsequent body landmark container and/or body language container received from the first device into a local copy of the synthetic body generator—stored in local memory on the second device—to generate a first stream of synthetic body images of the first user; and to then render this first stream of synthetic body images—with the first stream of synthetic face images of the first user—over the first background while playing back the first audio stream received from the first device.

In this variation, the second device can thus generate and render a first synthetic video feed—representing an authentic depiction of the first user's face, body, facial expressions, body posture, and body language—over the first background in near real-time during the video call.

Similarly, in this variation, the first device can generate and render a second synthetic video feed—representing an authentic depiction of the second user's face, body, facial expressions, and body posture—over the second background in near real-time during the video call.

11.4 Internal Synthetic Face Image Feed

In one variation, the first device can implement similar methods and techniques to locally generate a first synthetic video feed of the first user and to render this first synthetic video feed within the video call portal within the first instance of the application executing on the first device, thereby enabling the first user to visualize how she is seen by the second user during the video call.

For example, during the video call, the first device can render the first background—adjacent the second background—in the video call portal within the first instance of the application executing on the second device. Upon extraction of a facial landmark and expression container pair from a next frame in the first video feed, the first device can: insert the facial landmark and expression container pair and the first face model of the first user into a local copy of the synthetic face generator—stored in local memory on the first device—to generate a synthetic face image; and render the synthetic face image over the first background within the video call portal while concurrently rendering a second synthetic face image of the second user over the second background.

11.5 Video Call Conclusion

Then, upon conclusion of the video call, the first device can delete local copies of the second face model, the second body model, and/or the second background; and the second device can similarly delete local copies of the first face model, the first body model, and/or the first background.

12. Variation: Third Synthetic Video Feed

In one variation, the first device detects a third face in the first video feed during the video call and selectively enables or mutes synthesis of images of the third face at the second device based on whether the first user confirms representation of the third face at the second device and/or whether a face model of the third face is available.

12.1 Third User Detection

In one implementation, the first device implements face detection techniques to detect discrete faces in the first video feed. Upon detecting a first face in the first video feed, the first device can: extract a first set of biometric data for the first face from the first video feed; identify the first user based on this first set of biometric data; generate a first feed of facial landmark and expression container pairs for the first face; and stream this first feed of facial landmark and expression container pairs—with a link to or other association with the first face model—to the second device for reconstruction into synthetic face images of the first user according to the first face model.

However, upon detecting a third face in the first video feed, the first device can prompt the first user at the first device to confirm representation of the third user in a first synthetic video feed generated and rendered at the second device. Then, if the first user declines representation of the third user in the first synthetic video feed at the second device, the first device can: continue to track the third face in the first video feed in order to distinguish the first and third faces in the first video feed; and withhold generation and transmission of a third feed of facial landmark and expression container pairs for the third face.

12.2 Third User Video Feed Confirmed

Alternatively, if the first user confirms representation of the third user in the first synthetic video feed at the second device, the first device (or the remote computer system) can execute methods and techniques described above to extract a third set of biometric data for the third face from the first video feed and to compare this third set of biometric data to biometric data affiliated with the first user's account. In response to failing to match the third set of biometric data to biometric data stored in the first user's account, the first device can scan secondary user accounts affiliated with the first user (e.g., a second account associated with the first user's spouse, children, parents, or calibration object-workers) for biometric data that match the third set of biometric data.

In response to failing to match the third set of biometric data to biometric data affiliated with these secondary accounts, the first device can scan others accounts—such as a population of user accounts stored in a remote database—for biometric data that match the third set of biometric data.

12.3 Third User Identified

Upon successfully identifying the third face as a third user, the first device (or the remote computer system) can prompt selection of a face model or a look model associated with the third user.

The first device can then: trigger the second device to load the third face model—selected for the third user at the first device—such as from a remote database of face models; track the third user's face in the first video feed; extract a third feed of facial landmark and expression container pairs for the third user's face from the first video feed; and stream this third feed of facial landmark and expression container pairs to the second device.

The second device can then implement methods and techniques described above: to inject the third face model and the third feed of facial landmark and expression container pairs into the synthetic face generator to generate a third feed of synthetic face images; and to render this third feed of synthetic face images—adjacent the first feed of synthetic face images—over the first background.

12.4 Third User Not Identified

Conversely, if the first device (or the remote computer system) fails to successfully identify the third user but the first (or third) user confirms representation of the third user in the first synthetic video feed at the second device, the first device (or the remote computer system) can implement methods and techniques described above to automatically: extract a set of authentic face images of the third face from the first video feed; generate a new face model for the third face based on this set of authentic face images; and transmit the new face model for the third face to the second device. Throughout the process, as the first device (or the remote computer system) generates this new face model for the third face, the first device can stream a live video feed to the second device, which the second device can render directly. Once the first device (or the remote computer system) generates this new face model for the third face, the first device can transition to streaming feeds of facial landmark and expression container pairs for the first and third faces to the second device. The second device can then: implement face models for the first and third faces and these facial landmark and expression container feeds to generate first and third synthetic face image feeds; and render these first and third synthetic face image feeds over the first background.

Alternatively, as the first device (or the remote computer system) generates this new face model for the third face, the first device can generate and stream both the first and third facial landmark and expression container feeds to the second device. The second device can: transform the first face model for the first user and the first feed of facial landmark and expression container pairs into a first synthetic face image feed that mimics the first user's face depicted in the first video feed; and render this first synthetic face image feed over the first background. Concurrently, the second device can: implement a generic face model (e.g., for a cartoon character, a cat, a dog, a mouse) to transform the third feed of facial landmark and expression container pairs into a third synthetic face image feed that mimics a generic face (e.g., the cartoon character, the cat, the dog, the mouse); and render this third synthetic face image—adjacent the first synthetic face image feed—over the first background. In this implementation, once the first device (or the remote computer system) generates this new face model for the third face, the second device can download this new face model and transition to generating the third synthetic face image feed according to this new face model rather than the generic face model.

12.5 Third Face Model Preservation

Upon conclusion of the video call, the first and second devices can delete and discard the new face model for the third face.

Alternatively, the first device can prompt the first user to link the new face model to her account, thereby enabling the first device to quickly identify the third user, retrieve this new face model for the third user, and support generation of a synthetic video feed depicting both the first user and third user during a future video call with another device. Then, if the first user confirms this option, the first device (or the remote computer system) can generate a secondary account for the third user and store the new face model in the secondary account.

However, the first device, the second device, and/or the remote computer system can implement any other method or technique to generate feeds of facial landmark and expression container pairs for multiple faces depicted in a video feed and to simultaneously reconstruct these feeds of facial landmark and expression container pairs into a synthetic video feed containing photorealistic representations of these multiple faces, including the appearances, facial expressions, and relative positions of the faces depicted in the original video feed.

13. Multi-Party Video Call

In another variation shown in FIGS. 2A-2D, a multiple devices—such as including the first device, the second device, and a third device, etc.—concurrently execute the foregoing methods and techniques to host a multi-party video call in which each device in the video call transmits a feed of facial landmark and expression container pairs to other devices in the video call and generates and renders synthetic face images based on facial landmark and expression container feeds and face models received from these other devices in the video call.

In one implementation, the first and second devices similarly transmit first and second facial landmark and expression container feeds to a third device during a video call. The third device can then implement the first and second face models for the first and second users to concurrently transform the first and second facial landmark and expression container feeds into first and second synthetic face image feeds and then concurrently render these first and second synthetic face image feeds during the video call. The first device can implement similar methods and techniques to generate and render second and third synthetic face image feeds based on second and third face models of the second and third users and based on facial landmark and expression container feeds received from the second and third devices. The second device can further implement these methods and techniques to generate and render first and third synthetic face image feeds based on the first and third face models and based on facial landmark and expression container feeds received from the first and third devices.

In this variation, the first user may also elect different face or look models, body models, and/or backgrounds to distribute to other devices within the multi-party video call such that these devices generate synthetic video feeds depicting the first user with the same facial expressions and face pose but with different skin tone, facial hair, makeup, hair style, jewelry, and/or clothing, etc. in different spaces throughout the video call, as shown in FIGS. 2A-2D.

14. Expression Control

Figure 5:
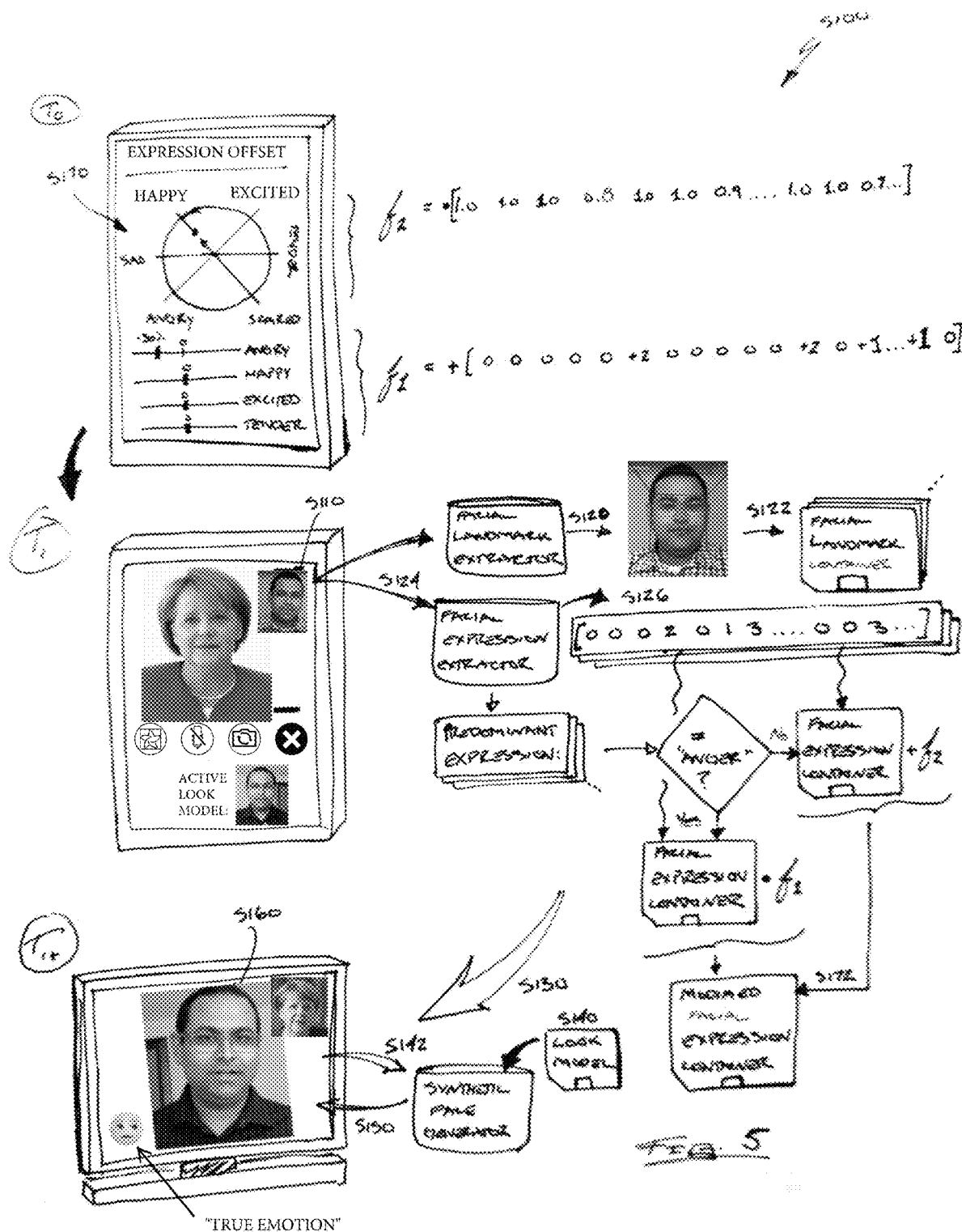
FIG. 5 is a flowchart representation of one variation of the method.

One variation of the method S100 shown in FIG. 5 includes: receiving a command from the first user to attenuate a target facial expression, in a synthetic video feed of synthetic face images of the first user, by a target magnitude in Block S170; interpreting a first facial expression of the first user, depicted in the first frame, based on intensities of the predefined set of action units stored in the first facial expression container; and, based on the command and in response to the facial expression corresponding to the target facial expression, reducing intensities of the predefined set of action units stored in the first facial expression container according to the target magnitude in Block S172.

In this variation, the method S100 can similarly include: receiving a command from the first user to amplify a target facial expression, in a synthetic video feed of synthetic face images of the first user, by a target magnitude in Block S170; interpreting a first facial expression of the first user, depicted in the first frame, based on intensities of the predefined set of action units stored in the first facial expression container; and, based on the command and in response to the facial expression corresponding to the target facial expression, increasing intensities of the predefined set of action units stored in the first facial expression container according to the target magnitude in Block S172.

In this variation, the method S100 can also include: receiving a command from the first user to attenuate all facial expressions, in a synthetic video feed of synthetic face images of the first user, by a target magnitude in Block S170; and decreasing intensities of representations of the first set of facial muscle actions stored in the first facial expression container according to the target magnitude based on the command in Block S172.

Furthermore, in this implementation, the method S100 can include: receiving a command from the first user to amplify all facial expressions, in a synthetic video feed of synthetic face images of the first user, by a target magnitude in Block S170; and increasing intensities of representations of the first set of facial muscle actions stored in the first facial expression container according to the target magnitude based on the command in Block S172.

Generally, in this variation, the device can execute Block S170 to record a preference from the user to shift an expression represented in a feed of facial expression containers—derived from a video feed of the user—from the user's true expression depicted in this video, such as: toward a particular expression; away from a particular expression; toward more animated expressions generally; or toward less animated expressions generally. The device can then execute Block S172 to modify facial expression containers (e.g., by increasing or decrease intensities of muscle actions represented in these facial expression containers) according to this preference.

14.1 Expression Control

In one implementation, before and/or during a video call, a first device: renders an expression offset menu; interfaces with the first user to record preferences for baseline expression, baseline expression intensity, maximum expression intensity, and/or minimum expression intensity, etc. from the user; and generates an expression offset function that captures these preferences entered by the first user. Then, during the video call, the first device can: access a video frame;

derive a facial landmark container and a facial expression container from the video frame; and revise a set of action units in the facial expression container according to the expression offset function, such as by incrementing intensities of action units corresponding to a baseline expression selected by the first user or decrementing intensities of action units corresponding to the expression selected for suppression or attenuation by the first user. The first device can then transmit this facial expression container—now with revised action units—to the second device. Accordingly, the second device can construct a synthetic face image based on this facial expression container, which depicts the first user: with facial landmarks aligned to facial landmarks depicted in the original video frame; with facial muscle actions deviating from the facial muscle actions depicted in the original video frame according to the expression offset function; and with a hair style, clothing, and/or adornment, etc. as represented by a look model selected by the first user.

In one example implementation, the first device presents—to the first user—an expression map containing multiple expression sectors, such as including "happy," "surprised," "bad," "fearful," "angry," "disgusted," and "sad" (and corresponding emotion sub-categories) sectors arranged in a 2D circular emotion pallete. In this example, the first device can initially locate a marker at the center of the expression map, which corresponds to a null expression offset function.

Then, if the first user moves marker toward the "happy" sector in the expression map, such as if the user desires to appear happier to others in the video call, the first device can calculate an expression offset that amplifies baseline intensities of action units corresponding to "happy" facial expressions. For example, the first device can populate the expression offset function with a set of intensities that are added to a combination of action units—in a facial expression container—that correspond to a "happy" facial expression, wherein these intensities are proportional to a distance from the center of the expression map to the marker now occupying the "happy" sector the expression map.

Similarly, if the first user moves the marker toward a "surprised" sector in the expression map, such as if the user desires to appear more excited to others in the video call, the first device can calculate an expression offset function that amplifies the baseline intensities of action units corresponding to "surprised" facial expression. For example, the first device can populate the expression offset function with a set of intensities that are added to a combination of action units—in a facial expression container—that correspond to a "surprised" facial expression, wherein these intensities are proportional to a distance from the center of the expression map to the marker now occupying the "surprised" sector the expression map.

Additionally or alternatively, the first device can render a set of slider bars, each corresponding to one primary emotion (e.g., "joy," "excitement," "surprise," "sadness," "anger," "disgust," "contempt," and/or "fear") and each including a slider initially located in a center (or "neutral") position. The first user may then: move a slider in a positive direction to trigger amplification of the corresponding expression; or move the slider in a negative direction to trigger attenuation of this expression. For example, if the first user moves a slider on the "anger" slider bar in the negative direction, the first device can calculate an expression offset function that attenuates (i.e., suppresses, reduces, scales down) intensities of action units corresponding to "angry" facial expressions, such as by a magnitude proportional to a distance from center of the slider bar to the slider.

More specifically, in this example, the first device can populate the expression offset with a set of intensity coefficients less than "1.0" (e.g., 0.85) that are multiplied by a combination of action units—in a facial expression container—that indicate an "angry" facial expression, wherein these intensity coefficients are a function of the distance from the slider to the center of the slider bar.

In a similar example, if the first user moves a slider on the "excitement" slider bar in the positive direction, the first device can calculate an expression offset function that amplifies (i.e., increases, scales up) intensities of action units corresponding to "excited" facial expressions, such as by a magnitude proportional to a distance from the center of the slider bar to the slider. More specifically, in this example, the first device can populate the expression offset with a set of intensity coefficients greater than "1.0" (e.g., 1.15) that are multiplied by a combination of action units—in a facial expression container—that indicate an "excited" facial expression, wherein these intensity coefficients are a function of the distance from the slider to the center of the slider bar.

14.2 Example: Excitement Reduction

In one example, the first user elects to reduce intensity of "excited" expressions represented in a synthetic video feed rendered for another user on the video call, such as: when the first user is preparing for a video call with a second user before a first date; or when the first user is entering a video call with her partner when her partner is on his way to a location of his surprise birthday party. In this example, the first user may move the slider on the "excitement" slider bar in a negative direction, such as to an "80%" position or to a "20% reduction" position. Accordingly, the first device can generate an expression offset function that: reduces intensity of the cheek raise action unit "6" (e.g., from activation of the orbicularis oculi muscle) by 10%; reduces intensity of the lip corner pull action unit "12" (e.g., from activation of the zygomaticus major muscle) by 20%; reduces intensity of the dimple action unit "14" (e.g., from activation of the buccinator muscle) by 30%; and reduces intensity of the mouth stretch corner pull action unit "27" (e.g., from activation of the pterygoids and digastric muscles muscles) by 20%.

The first device can then apply this expression offset function to all facial expression containers generated while this "excitement reduction" option is active during the video call.

Alternatively, during this video call, the first device can: access a video frame from the first video feed captured at the first device; implement methods and techniques described above to derive a facial landmark container and a facial expression container from this video frame; and implement an expression model to interpret a predominant expression type represented in this facial expression container—and therefore present on the first user's face at the time the video frame was captured. Then, if this predominant expression type is other than "excited," the first device can pass this facial expression container unchanged to the second device. However, if this predominant expression type is (or is analogous to) "excited," the first device can apply the expression offset function to the facial expression container to reduce the intensity of "excited" represented in the facial expression container and then transmit this modified facial expression container to a second device. The second device can then generate and render a synthetic face image based on this facial expression container.

14.3 Example: Anger Reduction+Happiness Augmentation

In another example, the first user elects to reduce intensity of "angry" expressions and increase intensity of "happy"

expressions represented in a synthetic video feed rendered for another user on the video call, such as when the first user is: having a bad day but preparing for an important business call; having a bad day but preparing for a video call with her child; or preparing for a video call with a business partner she dislikes. In this example, the first user may move the slider on the "anger" slider bar in a negative direction, such as to a "70%" position or to a "30% reduction" position. Similarly, the first user may move the maker on the expression map into the "happy" sector, such as to a "20% increase" position.

Accordingly, the first device can generate a first expression offset function that reduces intensity of "anger" represented by: reducing intensity of the brow lower action unit "4" (e.g., from activation of the depressor glabellae, depressor supercilii, and corrugator supercilii muscles) by 20%; reducing intensity of the lid tightening action unit "7" (e.g., from activation of the orbicularis oculi muscle) by 10%; and reducing intensity of the lip tighten action unit "23" (e.g., from activation of the orbicularis oris muscle) by 30%. Similarly, the first device can generate a second expression offset function that increases intensity of "happiness" represented by: increasing baseline intensity of the cheek raise action unit "6" (e.g., from activation of the orbicularis oculi muscle) from "0" to "B"; increasing baseline intensity of the lip corner pull action unit "12" (e.g., from activation of the zygomaticus major muscle) from "0" to "B"; increasing baseline intensity of the dimple action unit "14" (e.g., from activation of the buccinator muscle) from "0" to "A"; and increasing baseline intensity of the mouth stretch corner pull action unit "27" (e.g., from activation of the pterygoids and digastric muscles muscles) from "0" to "A."

The first device can then apply this expression offset function to all facial expression containers generated while this "excitement reduction" option is active during the video call.

Alternatively, during this video call, the first device can: access a video frame from the first video feed captured at the first device; implement methods and techniques described above to derive a facial landmark container and a facial expression container from this video frame; and implement an expression model to interpret a predominant expression type represented in this facial expression container—and therefore present on the first user's face at the time the video frame was captured. Then, if this predominant expression type is other than "angry," the first device can: apply the second expression offset function to the facial expression container only to increase the intensity of "happiness" represented in the facial expression container and then transmit this modified facial expression container to the second device. However, if this predominant expression type is (or is analogous to) "angry," the first device can: apply the first expression offset function to the facial expression container to reduce the intensity of "excited" represented in the facial expression container; (apply the second expression offset function to the facial expression container to increase the intensity of "happy" represented in this modified facial expression container;) and then transmit this modified facial expression container to second device. The second device can then generate and render a synthetic face image based on this facial expression container.

14.4 Example: Emotion Intensity Reduction

In another example, the first user elects to reduce all emotion intensities, such as if the first user exhibits an excitable personality but is preparing for an important business call. In this example, the first user may move the sliders for all expressions in a negative direction, such as to a "70%" position or to a "30% reduction" position.

Accordingly, the first device can generate an expression offset function that reduces intensities of all action units in a facial expression container by 30%. The first device can then apply this expression offset function to all facial expression containers generated while this "emotion intensity reduction" option is active during the video call.

14.5 Example: Emotion Intensity Amplification

In yet another example, the first user elects to increase all emotion intensities, such as if the first user is minimally expressive and selects this option in order to appear more expressive to others on a video call and thus improve emotional signaling to and communication with others on this video call. In this example, the first user may move the sliders for all expressions in a position direction, such as to a "130%" position or to a "30% increase" position.

Accordingly, the first device can generate an expression offset function that increases intensities of all action units in a facial expression container by 30%. The first device can then apply this expression offset function to all facial expression containers generated while this "emotion intensity increase" option is active during the video call.

14.6 Example: Boredom Limit

In another example, the first user elects to set a maximum intensity of "bored" expressions represented in a synthetic video feed rendered for another user on the video call, such as: when the first user is preparing for a recurring business video call that is historically tedious. In this example, the first user may activate and set a maximum expression intensity marker at a "40% of maximum" position on a "bored" slider bar. Accordingly, the first device can generate an expression offset function that resets limits for intensities of a combination of action units—indicating a "bored" expression—to 40% of their maximum possible intensities (e.g., an intensity limit of "2" given a maximum intensity of "5" and a maximum expression intensity marker at the "40% of maximum" position on the "bored" slider bar).

The first device can then apply this expression offset function to all facial expression containers generated while this "excitement reduction" option is active during the video call.

Alternatively, during this video call, the first device can: access a video frame from the first video feed captured at the first device; implement methods and techniques described above to derive a facial landmark container and a facial expression container from this video frame; and implement an expression model to interpret a predominant expression type represented in this facial expression container—and therefore present on the first user's face at the time the video frame was captured. Then, if this predominant expression type is other than "bored," the first device can pass this facial expression container unchanged to the second device. However, if this predominant expression type is (or is analogous to) "bored," the first device can apply the expression offset function to the facial expression container to reduce the intensity of "bored" represented in the facial expression container, including resetting the intensities of any action units in this facial expression container that indicate "bored" to the intensity limits specified in the expression offset function. The first device can then transmit this modified facial expression container to second device. The second device can then generate and render a synthetic face image based on this facial expression container.

14.7 Authentic Emotion Indicator

Therefore, the first device can modify the facial expression container such that reconstruction of a synthetic face image with the facial expression container depicts the first user with an expression (or emotion, "mood") that differs from the first user's true expression at the time the corresponding video frame was captured.

However, in the foregoing implementations and examples, the first device can also pair a facial expression container with a value (e.g., a tag) of the authentic expression (or emotion, "mood") exhibited by the first user at the time the corresponding video frame was captured. For example and as shown in FIG. 5, the first device can write this true expression value to the facial expression container or transmit this true expression value separately to the second device. The second device can then concurrently render: an emoticon (or "emoji"), avatar, or other iconography representative of the true expression value; and the synthetic face image generated from the concurrent facial expression container. The first and second devices can cooperate to enable the second user to both: view the first user as she desires to be seen by the first user; monitor the first user's true emotion or mood.

14.8 Presets

In the foregoing implementations and examples, the first device can store a set of preset expression control configurations, such as predefined for all users or customized by the first user prior to the video call and described emotion-based modifications to facial expression containers generated for the user. Thus, before or during a video call, the first user can select a preset expression control configuration from this set to apply to all video frames captured at the first device during the video call.

15. Local Synthetic Face Image Generation

In one variation of the method S100, the first device: accesses a video frame or an image, such as from a local live video feed; derives a facial landmark container and a facial expression container from this frame; and locally implements the synthetic face generator to transform this facial landmark container, this facial expression container, and a face model selected by the first user into a synthetic face image. The first device can then transmit this synthetic face image to other devices in a video call. For example, the first device can transition to local generation of a synthetic video feed in response to a quantity of users on the video call exceeding a threshold count (e.g., four users) in order to reduce computation at each other device in this video call to generate identical synthetic video feeds from facial landmark and expression container pairs received from the first device.

16. Synchronous v. Asynchronous Synthetic Video

Generally, the method is described here as executed by two devices: to stream facial landmark and expression containers derived from live video feeds of their users to the other device; and to locally reconstruct synthetic video feeds of the other users based on look models, facial landmark containers, and expression containers received from the other device during a live video call. More specifically, the method is thus described herein as executed by devices for real-time, synchronous video chat.

However, the method can additionally or alternatively be executed by similarly devices for asynchronous synthetic video messaging. For example, a first device can implement methods and techniques described above to: capture a video clip of a first user; interface with the first user to edit or modify the video clip; implement methods and techniques described above to extract a sequence of facial landmark and expression containers from this edited video clip; and transmit this sequence of facial landmark and expression containers to a second device associated with a second user selected by the first user, such as within an asynchronous synthetic video messaging platform. The second device can then: access a copy of a look model selected by the first user; insert the sequence of facial landmark and expression containers and the look model into a local copy of the synthetic face generator to generate a synthetic video clip depicting the user according to the original video clip; and then render this synthetic video clip for the second user, such as within a public or private message feed between the first and second users within the asynchronous synthetic video messaging platform.

The systems and methods described herein can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a human annotator computer or mobile device, wristband, smartphone, or any suitable combination thereof. Other systems and methods of the embodiment can be embodied and/or implemented at least in part as a machine configured to receive a computer-readable medium storing computer-readable instructions. The instructions can be executed by computer-executable components integrated by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor but any suitable dedicated hardware device can (alternatively or additionally) execute the instructions.

As a person skilled in the art will recognize from the previous detailed description and from the figures and claims, modifications and changes can be made to the embodiments of the invention without departing from the scope of this invention as defined in the following claims.

We claim:

1. A method comprising:
   during a setup period:
      accessing a target image of a first user;
      detecting a target face in the target image;
      representing a target constellation of facial landmarks, detected in the target image, in a target facial landmark container;
      representing a target set of facial muscle actions, detected in the target image, in a target facial expression container;
      generating a target set of face model coefficients;
      transforming the target facial landmark container, the facial expression container, and the target set of face model coefficients into a target synthetic face image according to a synthetic face generator;
      characterizing a difference between the target synthetic face image and the target face detected in the target image;
      adjusting the target set of face model coefficients to reduce the difference; and
      generating a first face model, associated with the first user, based on the target set of face model coefficients;
   during an operating period succeeding the setup period:
      accessing a first video feed depicting the first user;

receiving a first command, from the first user, to modify intensities of facial expressions by a target magnitude;

generating a first expression offset function based on the target magnitude;

for a first frame, in the first video feed, captured at a first time:

detecting a first constellation of facial landmarks in the first frame;

representing the first constellation of facial landmarks in a first facial landmark container;

detecting a first set of facial muscle actions in the first frame; and representing the first set of facial muscle actions in a first facial expression container by:

encoding the first set of facial muscle actions into a first set of action units; and encoding the first set of facial muscle actions into a first set of action intensities;

modifying intensities of facial muscle actions stored in the first facial expression container according to the first expression offset function; and transforming the first facial landmark container, the first facial expression container, and the first face model into a first synthetic face image according to the synthetic face generator; and rendering the first synthetic face image depicting the first user.

2. The method of claim 1, wherein detecting the first constellation of facial landmarks in the first frame and representing the first constellation of facial landmarks in the first facial landmark container comprise:

detecting a face in a first region of the first frame;

initializing the first facial landmark container; and for each facial landmark type in a predefined set of facial landmark types:

scanning the first region of the first frame for features analogous to the facial landmark type;

in response to detecting a feature analogous to the facial landmark type, extracting a location of the feature in the first frame; and writing the location of the feature, extracted from the first frame, to a position in the first facial landmark container corresponding to the facial landmark type.

3. The method of claim 1, wherein detecting the first set of facial muscle actions in the first frame and representing the first set of facial muscle actions in the first facial expression container comprise:

detecting a face in a first sector of the first frame;

initializing the first facial expression container; and for each action unit, in a predefined set of action units in the first set of action units representing action of human facial muscles:

detecting a facial region, depicted in the first sector of the first frame, containing a muscle associated with the action unit;

interpreting an intensity of action of the muscle based on a set of features extracted from the facial region depicted in the first sector of the first frame; and writing the intensity of action of the muscle to a position in the first facial expression container corresponding to the action unit.

4. The method of claim 3:

wherein receiving the first command comprises receiving the first command from the first user to attenuate a target facial expression, in a synthetic video feed of synthetic face images of the first user, by a target magnitude;

further comprising interpreting a first facial expression of the first user, depicted in the first frame, based on intensities of the predefined set of action units stored in the first facial expression container; and wherein modifying intensities of facial muscle actions stored in the first facial expression container according to the first expression offset function comprises, based on the first command and in response to the facial expression corresponding to the target facial expression, reducing intensities of the predefined set of action units stored in the first facial expression container according to the target magnitude.

5. The method of claim 3:

wherein receiving the first command comprises receiving the first command from the first user to amplify a target facial expression, in a synthetic video feed of synthetic face images of the first user, by a target magnitude;

further comprising interpreting a first facial expression of the first user, depicted in the first frame, based on intensities of the predefined set of action units stored in the first facial expression container; and wherein modifying intensities of facial muscle actions stored in the first facial expression container according to the first expression offset function comprises, based on the first command and in response to the facial expression corresponding to the target facial expression, increasing intensities of the predefined set of action units stored in the first facial expression container according to the target magnitude.

6. The method of claim 1:

wherein receiving the first command comprises receiving the first command from the first user to attenuate all facial expressions, in a synthetic video feed of synthetic face images of the first user, by a target magnitude; and wherein modifying intensities of facial muscle actions stored in the first facial expression container according to the first expression offset function comprises decreasing intensities of representations of the first set of facial muscle actions stored in the first facial expression container according to the target magnitude based on the first command.

7. The method of claim 1:

wherein receiving the first command comprises receiving the first command from the first user to amplify all facial expressions, in a synthetic video feed of synthetic face images of the first user, by a target magnitude; and wherein modifying intensities of facial muscle actions stored in the first facial expression container according to the first expression offset function comprises increasing intensities of representations of the first set of facial muscle actions stored in the first facial expression container according to the target magnitude based on the first command.

8. The method of claim 1:

wherein representing the target constellation of facial landmarks, detected in the target image, in the target facial landmark container comprises:

initializing the target facial landmark container;

for each facial landmark type in a predefined set of facial landmark types:

scanning the target image for features analogous to the facial landmark type;

in response to detecting a feature analogous to the facial landmark type, characterizing a position of the feature in the target image; and
representing the position of the feature in the target facial landmark container; and
wherein representing the target set of facial muscle actions, detected in the target image, in the target facial expression container comprises:
initializing the first facial expression container; and
for each action unit, in a predefined set of action units in the first set of action units representing action of human facial muscles:
detecting a facial region, depicted in the target image, containing a muscle associated with the action unit;
interpreting an intensity of action of the muscle based on a set of features extracted from the facial region depicted in the target image; and
representing the intensity of action of the muscle in the target facial expression container.

9. The method of claim 8:
further comprising:
accessing a video clip of the user; and
for each frame in a set of frames in the video clip:
detecting the face in a secondary region of the frame;
characterizing positions of a secondary set of features, analogous to facial landmark types in the predefined set of facial landmark types, detected in the secondary region of the frame;
representing positions of the secondary set of features in a secondary facial landmark container;
characterizing intensities of actions of a set of muscles, associated with by the predefined set of action units, detected in the secondary region of the frame;
representing intensities of actions of the set in a secondary facial expression container;
defining a secondary set of face model coefficients;
transforming the secondary facial landmark container, the secondary facial expression container, and the secondary set of face model coefficients into a secondary synthetic face image according to the synthetic face generator;
characterizing a secondary difference between the secondary synthetic face image and the secondary region of the frame depicting the face; and
adjusting the secondary set of face model coefficients to reduce the secondary difference; and
wherein generating the first face model comprises calculating the first face model based on a combination of:
the target set of face model coefficients; and
secondary sets of face model coefficients associated with the set of frames.

10. The method of claim 9:
wherein accessing the target image comprises accessing the target image representing a physiognomy preferred by the first user;
further comprising:
assigning a target weight to the target set of face model coefficients; and
for each frame in the set of frames in the video clip, assigning a secondary weight, less than the target weight, to the secondary set of face model coefficients associated with the frame; and
wherein generating the first face model comprises calculating the first face model based on a combination of:
the target set of face model coefficients weighted according to the target weight; and
the secondary set of face model coefficients, weighted according to secondary weights, associated with the set of frames.

11. The method of claim 1:
wherein accessing the first video feed comprises, at the first device, accessing the first video feed captured by a camera, coupled to the first device, during a video call within the operating period;
wherein transforming the first facial landmark container, the first facial expression container, and the first face model into the first synthetic face image according to the synthetic face generator comprises transforming the first facial landmark container, the first facial expression container, and the first face model into the first synthetic face image according to the synthetic face generator at the first device during the video call; and
further comprising:
at the first device, transmitting the first synthetic face image to a second device during the video call; and
at the second device, displaying the first synthetic face image for the second user at approximately the first time.

12. The method of claim 1:
further comprising, at a first device associated with the first user and a second device associated with a second user, entering a video call during the operating period;
wherein accessing the first video feed comprises, at the first device, accessing the first video feed captured by a camera, integrated into the first device, during the video call;
further comprising:
at the second device, loading a local copy of the first face model prior to the video call; and
at the first device, transmitting the first facial landmark container and the first facial expression container to the second device during the video call;
wherein transforming the first facial landmark container, the first facial expression container, and the first face model into the first synthetic face image according to the synthetic face generator comprises transforming the first facial landmark container, the first facial expression container, and the first face model into the first synthetic face image according to the synthetic face generator at the second device; and
further comprising, at the second device, displaying the first synthetic face image for the second user at approximately the first time.

13. The method of claim 12, wherein displaying the first synthetic face image for the second user at approximately the first time comprises displaying the first synthetic face image at the second device within 500 milliseconds of the first time.

14. The method of claim 12, further comprising:
during a second setup period at the second device:
accessing a second target image of the second user;
detecting a second target face in the second target image;
representing a second target constellation of facial landmarks, detected in the second target image, in a second target facial landmark container;
representing a second target set of facial muscle actions, detected in the second target image, in a second target facial expression container;
generating a second target set of face model coefficients;

transforming the second target facial landmark container, the second facial expression container, and the second target set of face model coefficients into a second target synthetic face image according to the synthetic face generator;
characterizing a second difference between the second target synthetic face image and the second target face detected in the second target image;
adjusting the second target set of face model coefficients to reduce the second difference; and
generating a second face model, associated with the second user, based on the second target set of face model coefficients;
at the first device, loading a local copy of the second face model prior to the video call;
at the second device during the video call:
accessing a second video feed captured by a second camera, integrated into the second device;
for a second frame, in the second video feed, captured at approximately the first time:
detecting a second constellation of facial landmarks in the second frame;
representing the second constellation of facial landmarks in a second facial landmark container;
detecting a second set of facial muscle actions in the second frame; and
representing the second set of facial muscle actions in a second facial expression container; and
transmitting the second facial landmark container and the second facial expression container to the first device;
at the first device during the video call:
transforming the second facial landmark container, the second facial expression container, and the second face model into a second synthetic face image according to the synthetic face generator at the second device; and
displaying the second synthetic face image for the second user at approximately the second time.
15. A method comprising:
during a setup period:
accessing a target image of a first user;
detecting a first set of facial muscle actions in the target image;
representing a first set of facial muscle actions, detected in the target image, in a first facial expression container by encoding the first set of facial muscle actions into a first set of action units;
generating a first set of face model coefficients;
transforming the first facial expression container, and the first set of face model coefficients into a target synthetic face image according to a synthetic face generator;
characterizing a difference between the target synthetic face image and a target face detected in the target image;
adjusting the first set of face model coefficients to reduce the difference;
generating a first face model, associated with the first user, based on the first set of face model coefficients that have been adjusted; and
during an operating period succeeding the setup period:
accessing a first video feed depicting the first user;
generating a first feed of facial expression containers representing facial expressions detected in the first video feed;

receiving a first command from the first user to modify intensities of facial expressions by a first target magnitude;
based on the first command:
generating a first expression offset function based on the first target magnitude; and
modifying intensities of emotions represented of the first feed of facial expression containers according to the first expression offset function;
transforming the first feed of facial expression containers and the first face model into a first feed of synthetic face images according to the synthetic face generator; and
rendering the first feed of synthetic face images.
16. The method of claim 15:
further during the setup period:
receiving a second command from the first user to attenuate facial expressions, in the target image of the first user, by a second target magnitude;
based on the second command:
generating a second expression offset function based on the second target magnitude; and
modifying intensities of emotions represented in a second feed of facial expression containers according to the second expression offset function;
transforming the second feed of facial expression containers and the first face model into a second feed of synthetic face images according to the synthetic face generator; and
rendering the second feed of synthetic face images.
17. The method of claim 16, further comprising, during the setup period:
receiving a third command from the first user to amplify facial expressions, in the target image of the first user, by a third target magnitude;
based on the third command:
generating a third expression offset function based on the third target magnitude; and
modifying intensities of emotions represented in a third feed of facial expression containers according to the third expression offset function;
transforming the third feed of facial expression containers and the first face model into a third feed of synthetic face images according to the synthetic face generator; and
rendering the third feed of synthetic face images.
18. The method of claim 15, further comprising, during the operation period succeeding the setup period:
accessing the first video feed depicting the first user is performed by a first device;
transmitting by the first device, the first feed facial expression containers based on the first command containing the modified intensities of facial expressions, to a second device; and
constructing the first feed synthetic face images on the second device, based on the first feed facial expression containers transmitted to the second device, the first synthetic image, depicting facial muscle actions deviating from the first set of facial muscle actions detected in the target image.
19. A method comprising:
during a setup period:
accessing a target image of a first user;
detecting a first set of facial muscle actions in the target image;

representing a first set of facial muscle actions, detected in the target image, in a first facial expression container by encoding the first set of facial muscle actions into a first set of action units;

generating a first set of face model coefficients;

transforming the first facial expression container and the first set of face model coefficients into a target synthetic face image according to a synthetic face generator;

characterizing a difference between the target synthetic face image and a target face detected in the target image;

adjusting the first set of face model coefficients to reduce the difference; and generating a first face model, associated with the first user, based on the first set of face model coefficients that have been adjusted; and during an operating period succeeding the setup period:

accessing a first video feed depicting the first user;

accessing a first audio feed depicting speech of the first user;

interpreting a first emotion in the first audio feed;

representing the first emotion in a first facial expression container;

receiving a first command from the first user to modify intensities of facial expressions by a first target magnitude;

based on the first command, modifying an intensity of the first emotion, represented in the first facial expression container, according to the first target magnitude;

transforming the first facial expression container, the first facial expression container, and the first face model into a first synthetic face image according to the synthetic face generator; and constructing the first synthetic face image based on the revised first expression container with the revised first set of action units, to depict the first user.

20. The method of claim 19, further comprising, during the operation period succeeding the setup period:

accessing the first video feed depicting the first user is performed by a first device;

accessing the first audio feed depicting speech of the first user is performed by the first device;

transmitting by the first device, the first facial expression container based on the first command containing the modified intensities of facial expressions, to a second device;

verifying, by the second device, that the first facial expression container corresponds to the first emotion; and constructing the first synthetic face image on the second device, based on the first facial expression container transmitted to the second device, the first synthetic image, depicting facial muscle actions deviating from the first set of facial muscle actions detected in the target image.

* * * * *